(12) United States Patent
Muhammad et al.

(10) Patent No.: US 6,398,548 B1
(45) Date of Patent: **\*Jun. 4, 2002**

(54) METHOD AND SYSTEM FOR INCREMENTALLY MOVING TEETH

(75) Inventors: Chishti Muhammad, Sunnyvale, CA (US); Apostolos Lerios, Austin, TX (US); Brian Freyburger; Kelsey Wirth, both of Palo Alto, CA (US); Richard Ridgley, Los Altos, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/466,353

(22) Filed: Dec. 17, 1999

(Under 37 CFR 1.47)

Related U.S. Application Data

(63) Continuation of application No. PCT/US98/12861, filed on Jun. 19, 1998, which is a continuation of application No. 08/947,080, filed on Oct. 8, 1997, now Pat. No. 5,975,893.
(60) Provisional application No. 60/050,342, filed on Jun. 20, 1997.

(51) Int. Cl.[7] ................................................. A61C 3/00
(52) U.S. Cl. ............................................ 433/24; 433/6
(58) Field of Search .......................... 433/6, 8, 24, 213, 433/215

(56) References Cited

U.S. PATENT DOCUMENTS 3,916,526 A * 11/1975 Schudy ........................ 433/82
5,740,267 A *  4/1998 Echerer et al. ............. 382/132

OTHER PUBLICATIONS

Nahoum, H.I., "The vacuum formed dental contour appliance" *The New York State Dental Journal* (Nov. 1964) 30(9):385–390.

* cited by examiner

*Primary Examiner*—John J. Wilson
(74) *Attorney, Agent, or Firm*—Townsend & Townsend and Crew, LLP; Bao Tran

(57) ABSTRACT

A system for repositioning teeth comprises a plurality of individual appliances. The appliances are configured to be placed successively on the patient's teeth and to incrementally reposition the teeth from a initial tooth arrangement, through a plurality of intermediate tooth arrangements, and to a final tooth arrangement. The system of appliances is usually configured at the outset of treatment so that the patient may progress through treatment without the need to have the treating professional perform each successive step in the procedure.

71 Claims, 19 Drawing Sheets

METHOD AND SYSTEM FOR INCREMENTALLY MOVING TEETH

The present application is a which is a continuation of PCT/US 98/12861 filed Jun. 19, 1998, continuation of U.S. patent application Ser. No. 08/947,080; filed on Oct. 8, 1997, now U.S. Pat. No. 5,975,893, which claims priority from provisional application Ser. No. 60/050,342; filed on Jun. 20, 1997, the full disclosures of which are incorporated herein by reference.

BACKGROUND OF THE INVENTION

1. Field of the Invention

The present invention is related generally to the field of orthodontics. More particularly, the present invention is related to a method and system for incrementally moving teeth from an initial tooth arrangement to a final tooth arrangement.

Repositioning teeth for aesthetic or other reasons is accomplished conventionally by wearing what are commonly referred to as "braces." Braces comprise a variety of appliances such as brackets, archwires, ligatures, and O-rings. Attaching the appliances to a patient's teeth is a tedious and time consuming enterprise requiring many meetings with the treating orthodontist. Consequently, conventional orthodontic treatment limits an orthodontist's patient capacity and makes orthodontic treatment quite expensive.

Before fastening braces to a patient's teeth, at least one appointment is typically scheduled with the orthodontist, dentist, and/or X-ray laboratory so that X-rays and photographs of the patient's teeth and jaw structure can be taken. Also during this preliminary meeting, or possibly at a later meeting, an alginate mold of the patient's teeth is typically made. This mold provides a model of the patient's teeth that the orthodontist uses in conjunction with the X-rays and photographs to formulate a treatment strategy. The orthodontist then typically schedules one or more appointments during which braces will be attached to the patient's teeth.

At the meeting during which braces are first attached, the teeth surfaces are initially treated with a weak acid the acid optimizes the adhesion properties of the teeth surfaces for brackets and bands that are to be bonded to them. The brackets and bands serve as anchors for other appliances to be added later. After the acid step, the brackets and bands are cemented to the patient's teeth using a suitable bonding material. No force-inducing appliances are added until the cement is set. For this reason, it is common for the orthodontist to schedule a later appointment to ensure that the brackets and bands are well bonded to the teeth.

The primary force-inducing appliance in a conventional set of braces is the archwire. The archwire is resilient and is attached to the brackets by way of slots in the brackets. The archwire links the brackets together and exerts forces on them to move the teeth over time. Twisted wires or elastomeric O-rings are commonly used to reinforce attachment of the archwire to the brackets. Attachment of the archwire to the brackets is known in the art of orthodontia as "ligation" and wires used in this procedure are called "ligatures." The elastomeric O-rings are called "plastics."

After the archwire is in place, periodic meetings with the orthodontist are required, during which the patient's braces will be adjusted by installing a different archwire having different force inducing properties or by replacing or tightening existing ligatures. Typically, these meetings are scheduled every three to six weeks.

As the above illustrates, the use of conventional braces is a tedious and time consuming process and requires many visits to the orthodontist's office. Moreover, from the patient's perspective, the use of braces is unsightly, uncomfortable, presents a risk of infection, and makes brushing, flossing, and other dental hygiene procedures difficult.

For these reasons, it would be desirable to provide alternative methods and systems for repositioning teeth. Such methods and systems should be economical, and in particular should reduce the amount of time required by the orthodontist in planning and overseeing each individual patient. The methods and systems should also be more acceptable to the patient, in particular being less visible, less uncomfortable, less prone to infection, and more compatible with daily dental hygiene. At least some of these objectives will be met by the methods and systems of the present invention described hereinafter.

2. Description of the Background Art

Tooth positioners for finishing orthodontic treatment are described by Kesling in the *Am. J. Orthod. Oral. Surg.* 31:297–304 (1945) and 32:285–293 (1946). The use of silicone positioners for the comprehensive orthodontic realignment of a patient's teeth is described in Warunek et al. (1989) *J. Clin. Orthod.* 23:694–700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139.

other publications describing the fabrication and use of dental positioners include Kleemann and Janssen (1996) *J. Clin. Orthodon.* 30:673–680; Cureton (1996) *J. Clin. Orthodon.* 30:390–395; Chiappone (1980) *J. Clin. Orthodon.* 14:121–133; Shilliday (1971) *Am. J. Orthodontics* 59:596–599; Wells (1970) *Am. J. Orthodontics* 58:351–366; and Cottingham (1969) *Am. J. Orthodontics* 55:23–31.

Kuroda et al. (1996) *Am. J. Orthodontics* 110:365–369 describes a method for laser scanning a plaster dental cast to produce a digital image of the cast. See also U.S. Pat. No. 5,605,459.

U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the jaw is described in U.S. Pat. Nos. 5,342,202 and 5,340,309. Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

SUMMARY OF THE INVENTION

The present invention provides improved methods and systems for repositioning teeth from an initial tooth arrangement to a final tooth arrangement. Repositioning is accomplished with a system comprising a series of appliances configured to receive the teeth in a cavity and incrementally reposition individual teeth in a series of at least three successive steps, usually including at least four successive steps, often including at least ten steps, sometimes including at least twenty-five steps, and occasionally including forty or more steps. Most often, the methods and systems will reposition teeth in from ten to twenty-five successive steps, although complex cases involving many of the patient's teeth may take forty or more steps. The successive use of a number of such appliances permits each appliance to be configured to move individual teeth in small increments, typically less than 2 mm, preferably less than 1 mm, and more preferably less than 0.5 mm. These limits refer to the maximum linear translation of any point on a tooth as a result of using a single appliance. The movements provided by successive appliances, of course, will usually not be the same for any particular tooth. Thus, one point on a tooth may be moved by a particular distance as a result of the use of one appliance and thereafter moved by a different distance and/or in a different direction by a later appliance.

The individual appliances will preferably comprise a polymeric shell having the teeth-receiving cavity formed therein, typically by molding as described below. Each individual appliance will be configured so that its tooth-receiving cavity has a geometry corresponding to an intermediate or end tooth arrangement intended for that appliance. That is, when an appliance is first worn by the patient, certain of the teeth will be misaligned relative to an undeformed geometry of the appliance cavity. The appliance, however, is sufficiently resilient to accommodate or conform to the misaligned teeth, and will apply sufficient resilient force against such misaligned teeth in order to reposition the teeth to the intermediate or end arrangement desired for that treatment step.

Systems according to the present invention will include at least a first appliance having a geometry selected to reposition a patient's teeth from the initial tooth arrangement to a first intermediate arrangement where individual teeth will be incrementally repositioned. The system will further comprise at least one intermediate appliance having a geometry selective to progressively reposition teeth from the first intermediate arrangement to one or more successive intermediate arrangements. The system will still further comprise a final appliance having a geometry selected to progressively reposition teeth from the last intermediate arrangement to the desired final tooth arrangement. In some cases, it will be desirable to form the final appliance or several appliances to "over correct" the final tooth position, as discussed in more detail below.

As will be described in more detail below in connection with the methods of the present invention, the systems may be planned and all individual appliances fabricated at the outset of treatment, and the appliances may thus be provided to the patient as a single package or system. The order in which the appliances are to be used will be clearly marked, (e.g. by sequential numbering) so that the patient can place the appliances over his or her teeth at a frequency prescribed by the orthodontist or other treating professional. Unlike braces, the patient need not visit the treating professional every time an adjustment in the treatment is made. While the patients will usually want to visit their treating professionals periodically to assure that treatment is going according to the original plan, eliminating the need to visit the treating professional each time an adjustment is to be made allows the treatment to be carried out in many more, but smaller, successive steps while still reducing the time spent by the treating professional with the individual patient. Moreover, he ability to use polymeric shell appliances which are more comfortable, less visible, and removable by the patient, greatly improves patient compliance, comfort, and satisfaction.

According to a method of the present invention, a patient's teeth are repositioned from an initial tooth arrangement to a final tooth arrangement by placing a series of incremental position adjustment appliances in the patient's mouth. Conveniently, the appliances are not affixed and the patient may place and replace the appliances at any time during the procedure. The first appliance of the series will have a geometry selected to reposition the teeth from the initial tooth arrangement to a first intermediate arrangement. After the first intermediate arrangement is approached or achieved, one or more additional (intermediates appliances will be successively placed on the teeth, where such additional appliances have geometries selected to progressively reposition teeth from the first intermediate arrangement through successive intermediate arrangement(s). The treatment will be finished by placing a final appliance in the patient's mouth, where the final appliance has a geometry selected to progressively reposition teeth from the last intermediate arrangement to the final tooth arrangement. The final appliance or several appliances in the series may have a geometry or geometries selected to over correct the tooth arrangement, i.e. have a geometry which would (if fully achieved) move individual teeth beyond the tooth arrangement which has been selected as the "final." Such over correction may be desirable in order to offset potential relapse after the repositioning method has been terminated, i.e. to permit some movement of individual teeth back toward their pre-corrected positions. Over correction may also be beneficial to speed the rate of correction, i.e. by having an appliance with a geometry that is positioned beyond a desired intermediate or final position, the individual teeth will be shifted toward the position at a greater rate. In such cases, treatment can be terminated before the teeth reach the positions defined by the final appliance or appliances. The method will usually comprise placing at least two additional appliances, often comprising placing at least ten additional appliances, sometimes placing at least twenty-five additional appliances, and occasionally placing at least forty or more additional appliances. Successive appliances will be replaced when the teeth either approach (within a preselected tolerance) or have reached the target end arrangement for that stage of treatment, typically being replaced at an interval in the range from 2 days to 20 days, usually at an interval in the range from 5 days to 10 days.

Often, it may be desirable to replace the appliances at a time before the "end" tooth arrangement of that treatment stage is actually achieved. It will be appreciated that as the teeth are gradually repositioned and approach the geometry defined by a particular appliance, the repositioning force on the individual teeth will diminish greatly. Thus, it may be possible to reduce the overall treatment time by replacing an earlier appliance with the successive appliance at a time when the teeth have been only partially repositioned by the earlier appliance. Thus, the FDDS can actually represent an over correction of the final tooth position. This both speeds the treatment and can offset patient relapse.

In general, the transition to the next appliance can be based on a number of factors. Most simply, the appliances can be replaced on a predetermined schedule or at a fixed time interval (i.e. number of days for each appliance) determined at the outset based on an expected or typical patient response. Alternatively, actual patient response can be taken into account, e.g. a patient can advance to the next appliance when that patient no longer perceives pressure on their teeth from a current appliance, i.e. the appliance they have been wearing fits easily over the patient's teeth and the patient experiences little or no pressure or discomfort on his or her teeth. In some cases, for patients whose teeth are responding very quickly, it may be possible for a treating professional to decide to skip one or more intermediate appliances, i.e. reduce the total number of appliances being used below the number determined at the outset. In this way, the overall treatment time for a particular patient can be reduced.

In another aspect, methods of the present invention comprise repositioning teeth using appliances comprising polymeric shells having cavities shaped to receive and resiliently reposition teeth to produce a final tooth arrangement. The present invention provides improvements to such methods which comprise determining at the outset of treatment geometries for at least three of the appliances which are to be worn successively by a patient to reposition teeth from an initial tooth arrangement to the final tooth arrangement. Preferably, at least four geometries will be determined in the outset, often at least ten geometries, Frequently at least twenty-five geometries, and sometimes forty or more geometries. Usually, the tooth positions defined by the cavities in each successive geometry differ from those defined by the prior geometry by no more than 2 mm, preferably no more than 1 mm, and often no more than 0.5 mm, as defined above.

In yet another aspect, methods are provided for producing a digital data set representing a final tooth arrangement. The methods comprise providing an initial data set representing an initial tooth arrangement, and presenting a visual image based on the initial data set. The visual image is then manipulated to reposition individual teeth in the visual image. A final digital data set is then produced which represents the final tooth arrangement with repositioned teeth as observed in the visual image. Conveniently, the initial digital data set may be provided by conventional techniques, including digitizing X-ray images, images produced by computer-aided tomography (CAT scans), images produced by magnetic resonance imaging (MRI), and the like. Preferably, the images will be three-dimensional images and digitization may be accomplished using conventional technology. Usually, the initial digital data set is provided by producing a plaster cast of the patient's teeth (prior to treatment) by conventional techniques. The plaster cast so produced may then be scanned using laser or other scanning equipment to produce a high resolution digital representation of the plaster cast of the patient's teeth. Use of the plaster cast is preferred since it does not expose the patient to X-rays or subject the patient to the inconvenience of an MRI scan.

In a preferred embodiment, a wax bite is also obtained from the patient using standard methods. The wax bite allows plaster casts of a patient's upper and lower dentition to be placed relative to one another in the centric occlusal position. The pair of casts are then scanned to provide information on the relative position of the jaw in this position. This information is then incorporated into the IDDS for both arches.

Once the digital data set is acquired, an image can be presented and manipulated on a suitable computer system equipped with computer-aided design software, as described in greater detail below. The image manipulation will usually comprise defining boundaries about at least some of the individual teeth, and causing the images of the teeth to be moved relative to the jaw and other teeth by manipulation of the image via the computer. Methods are also provided for detecting cusp information for the teeth. The image manipulation can be done entirely subjectively, i.e. the user may simply reposition teeth in an aesthetically and/or therapeutically desired manner based on observation of the image alone. Alternatively, the computer system could be provided with rules and algorithms which assist the user in repositioning the teeth. In some instances, it will be possible to provide rules and algorithms which reposition the teeth in a fully automatic manner, i.e. without user intervention. Once the individual teeth have been repositioned, a final digital data set representing the desired final tooth arrangement will be generated and stored.

A preferred method for determining the final tooth arrangement is for the treating professional to define the final tooth positions, e.g. by writing a prescription. The use of prescriptions for defining the desired outcomes of orthodontic procedures is well known in the art. When a prescription or other final designation is provided, the image can then be manipulated to match the prescription. In some cases, it would be possible to provide software which could interpret the prescription in order to generate the final image and thus the digital data set representing the final tooth arrangement.

In yet another aspect, methods according to the present invention are provided for producing a plurality of digital data sets representing a series of discrete tooth arrangements progressing from an initial tooth arrangement to a final tooth arrangement. Such methods comprise providing a digital data set representing an initial tooth arrangement (which may be accomplished according to any of the techniques set forth above). A digital data set representing a final tooth arrangement is also provided. Such final digital data set may be determined by the methods described previously. The plurality of successive digital data sets are then produced based on the initial digital data set and the final digital data set. Usually, the successive digital data sets are produced by determining positional differences between selected individual teeth in the initial data set and in the final data set and interpolating said differences. Such interpolation may be performed over as many discrete stages as may be desired, usually at least three, often at least four, more often at least ten, sometimes at least twenty-five, and occasionally forty or more. Many times, the interpolation will be linear interpolation for some or all of the positional differences. Alternatively, the interpolation may be non-linear. In a preferred embodiment, non-linear interpolation is computed automatically by the computer using path scheduling and collision detection techniques to avoid interferences between individual teeth. The positional differences will correspond to tooth movements where the maximum linear movement of any point on a tooth is 2 mm or less, usually being 1 mm or less, and often being 0.5 mm or less.

Often, the user will specify certain target intermediate tooth arrangements, referred to as "key frames," which are incorporated directly into the intermediate digital data sets. The methods of the present invention then determine successive digital data sets between the key frames in the manner described above, e.g. by linear or non-linear interpolation between the key frames. The key frames may be determined by a user, e.g. the individual manipulating a visual image at the computer used for generating he digital data sets, or alternatively may be provided by the treating professional as a prescription in the same manner as the prescription for the final tooth arrangement.

In still another aspect, methods according to the present invention provide for fabricating a plurality of dental incremental position adjustment appliances. Said methods comprise providing an initial digital data set, a final digital data set, and producing a plurality of successive digital data sets representing the target successive tooth arrangements, generally as just described. The dental appliances are then fabricated based on at least some of the digital data sets representing the successive tooth arrangements. Preferably, the fabricating step comprises controlling a fabrication machine based on the successive digital data sets to produce successive positive models of the desired tooth arrangements. The dental appliances are then produced as negatives of the positive models using conventional positive pressure or vacuum fabrication techniques. The fabrication machine may comprise a stereolithography or other similar machine which relies on selectively hardening a volume of non-hardened polymeric resin by scanning a laser to selectively harden the resin in a shape based on the digital data set. Other fabrication machines which could be utilized in the methods of the present invention include tooling machines and wax deposition machines.

In still another aspect, methods of the present invention for fabricating a dental appliance comprise providing a digital data set representing a modified tooth arrangement for a patient. A fabrication machine is then used to produce a positive model of the modified tooth arrangement based on the digital data set. The dental appliance is then produced as a negative of the positive model. The fabrication machine may be a stereolithography or other machine as described above, and the positive model is produced by conventional pressure or vacuum molding techniques.

In a still further aspect, methods for fabricating a dental appliance according to the present invention comprise providing a first digital data set representing a modified tooth arrangement for a patient. A second digital data set is then produced from the first digital data set, where the second data set represents a negative model of the modified tooth arrangement. The fabrication machine is then controlled based on the second digital data set to produce the dental appliance. The fabrication machine will usually rely on selectively hardening a non-hardened resin to produce the appliance. The appliance typically comprises a polymeric shell having a cavity shape to receive and resiliently reposition teeth from an initial tooth arrangement to the modified tooth arrangement.

DESCRIPTION OF SPECIFIC EMBODIMENTS

According to the present invention, systems and methods are provided for incrementally moving teeth using a plurality of discrete appliances, where each appliance successively moves one or more of the patient's teeth by relatively small amounts. The tooth movements will be those normally associated with orthodontic treatment, including translation in all three orthogonal directions relative to a vertical centerline, rotation of the tooth centerline in the two orthodontic directions ("root angulation" and "torque"), as well as rotation about the centerline.

Figure 1A:
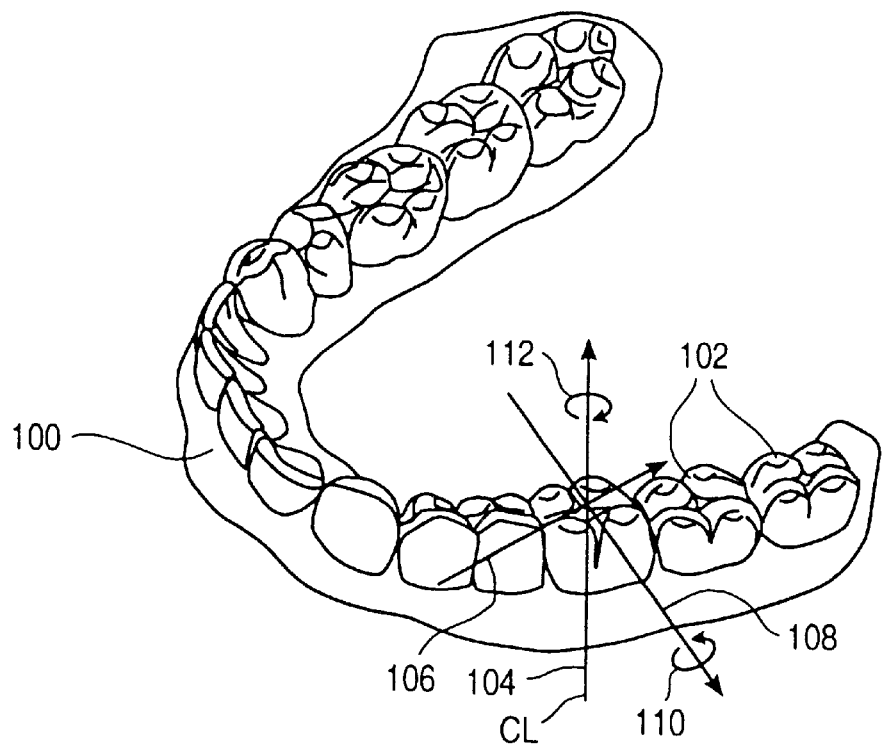
FIG. 1A illustrates a patient s jaw and provides a general indication of how teeth may be moved by the methods and apparatus of the present invention.
Figure 1B:
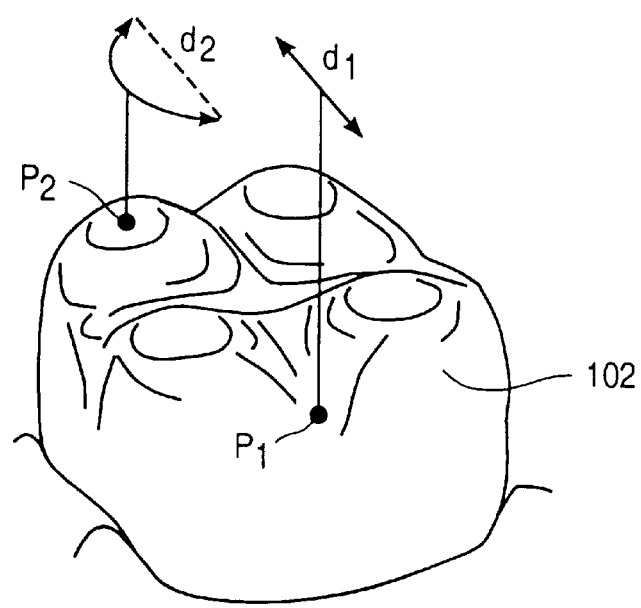
FIG. 1B illustrates a single tooth from FIG. 1A and defines how tooth movement distances are determined.

Referring now to FIG. 1A, a representative jaw 100 includes sixteen teeth 102. ,he present invention is intended to move at least some of these teeth from an initial tooth arrangement to a final tooth arrangement. To understand how the teeth may be moved, an arbitrary centerline (CL) is drawn through one of the teeth 102. With reference to this centerline (CL), the teeth may be moved in the orthogonal directions represented by axes 104, 106, and 108 (where 104 is the centerline). The centerline may be rotated about the axis 108 (root angulation) and 104 (torque) as indicated by arrows 110 and 112, respectively. Additionally, the tooth may be rotated about the centerline, as represented by arrow 114. Thus, all possible free-form motions of the tooth can be performed. Referring now to FIG. 1B, the magnitude of any tooth movement achieved by the methods and devices of the present invention will be defined in terms of the maximum linear translation of any point P on a tooth 102. Each point $P_i$ will undergo a cumulative translation as that tooth is moved in any of the orthogonal or rotational directions defined in FIG. 1A. That is, while the point will usually follow a non-linear path, there will be a linear distance between any point in the tooth when determined at any two times during the treatment. Thus, an arbitrary point $P_1$ may in fact undergo a true side-to-side translation as indicated by arrow $d_1$, while a second arbitrary point $P_2$ may travel along an arcuate path, resulting in a final translation $d_2$. Many aspects of the present invention are defined in terms of the maximum permissible movement of a point $P_i$ induced by the methods in any particular tooth. Such maximum tooth movement, in turn, is defined as the maximum linear translation of that point $P_i$ on the tooth which undergoes the maximum movement for that tooth in any treatment step.

Figure 1C:
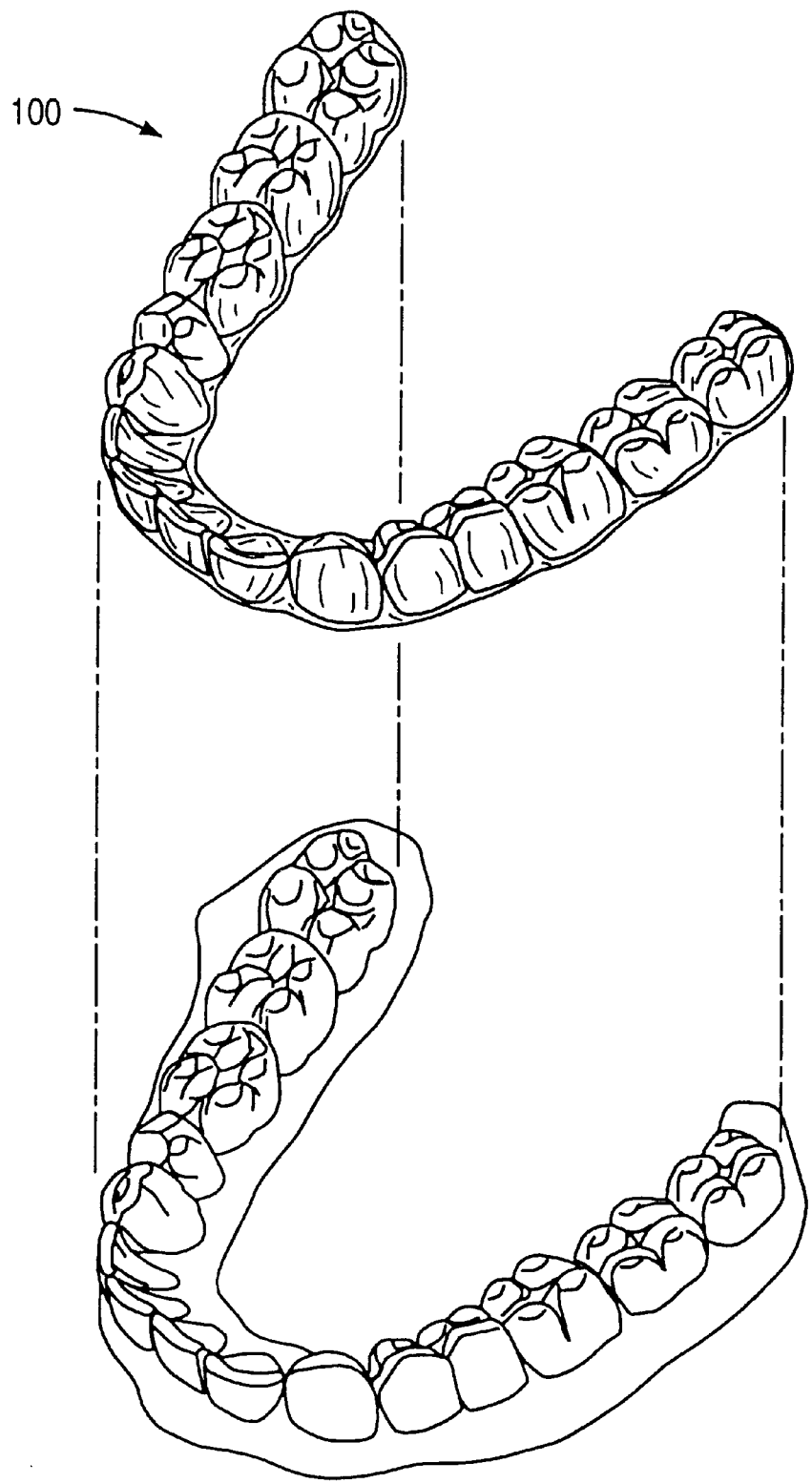
FIG. 1C illustrates the jaw of FIG. 1A together with an incremental position adjustment appliance which has been configured according to the methods of the present invention.

Referring now to FIG. 1C, systems according to the present invention will comprise a plurality of incremental position adjustment appliances. The appliances are intended to effect incremental repositioning of individual teeth in the jaw as described generally above. In a broadest sense, the methods of the present invention can employ any of the known positioners, retainers, or other removable appliances which are known for finishing and maintaining teeth positions in connection with conventional orthodontic treatment. The systems of the present invention, in contrast with prior apparatus and systems, will provide a plurality of such appliances intended to be worn by a patient successively in order to achieve the gradual tooth repositioning as described herein. A preferred appliance 100 will comprise a polymeric shell having a cavity shaped to receive and resiliently reposition teeth from one tooth arrangement to a successive tooth arrangement. The polymeric shell will preferably, but not necessarily, fit over all teeth present in the upper or lower jaw. Often, only certain one(s) of the teeth will be repositioned while others of the teeth will provide a base or anchor region for holding the repositioning appliance in place as it applies the resilient repositioning force against the tooth or teeth to be repositioned in complex cases, however, many or most of the teeth will be repositioned at some point during the treatment. In such cases, the teeth which are moved can also serve as a base or anchor region for holding the repositioning appliance. Additionally, the gums and/or the palette can serve as an anchor region, thus allowing all or nearly all of the teeth to be repositioned simultaneously.

The polymeric appliance 100 of FIG. 1C is preferably formed from a thin sheet of a suitable elastomeric polymeric, such as Tru-Tain 0.03 in thermal forming dental material, Tru-Tain Plastics, Rochester, Minn. 55902. Usually, no wires or other means will be provided for holding the appliance in place over the teeth. In some cases, however, it will be desirable or necessary to provide individual anchors on tee with corresponding receptacles or apertures in the appliance 100 so that the appliance can apply an upward force on the tooth which would not be possible in the absence of such an anchor. Specific methods for producing the appliances 100 are described hereinafter.

Figure 2:
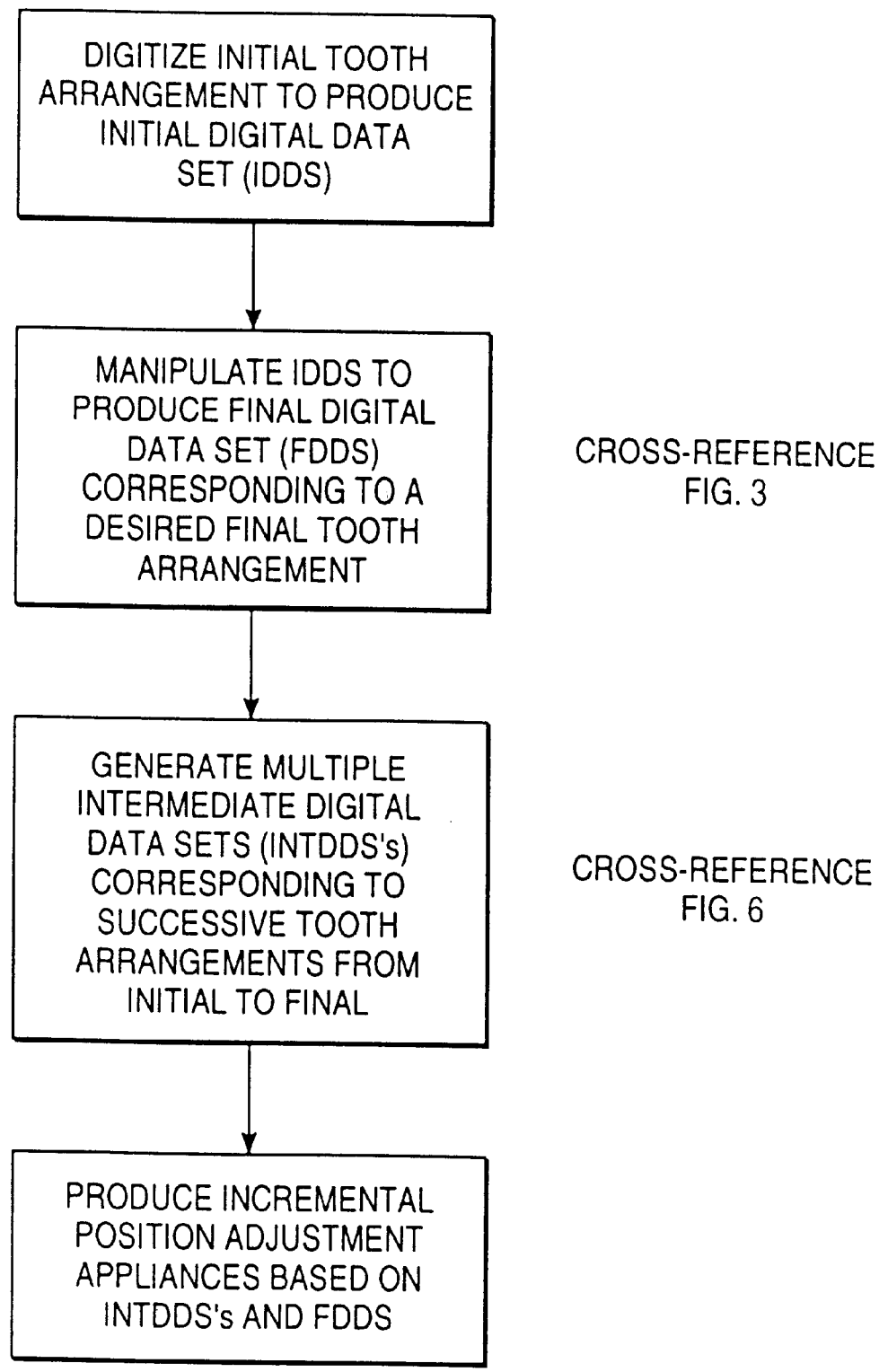
FIG. 2 is a block diagram illustrating the steps of the present invention for producing a system of incremental position adjustment appliances.

Referring now to FIG. 2, the overall method of the present invention for producing the incremental position adjustment appliances for subsequent use by a patient to reposition the patient's teeth will be described. As a first step, a digital data set representing an initial tooth arrangement is obtained, referred to hereinafter as the IDDS. The IDDS may be obtained in a variety of ways. For example, the patient's teeth may be scanned or imaged using well known technology, such as X-rays, three-dimensional X-rays, computer-aided tomographic images or data sets, magnetic resonance images, etc. Methods for digitizing such conventional images to produce data sets useful in the present invention are well known and described in the patent and medical literature. Usually, however, the present invention will rely on first obtaining a plaster cast of the patient's teeth by well known techniques, such as those described in Graber, *Orthodontics: Principle and Practice*. Second Edition, Saunders, Philadelphia, 1969, pp. 401–415. After the tooth casting is obtained, it can be digitally scanned using a conventional laser scanner or other range acquisition system to produce the IDDS. The data set produced by the range acquisition system may, of course, be converted to other formats to be compatible with the software which is used for manipulating images within the data set, as described in more detail below. General techniques for producing plaster casts of teeth and generating digital models using laser scanning techniques are described, for example, in U.S. Pat. No. 5,605,459, the full disclosure of which is incorporated herein by reference.

There are a variety of range acquisition systems, generally categorized by whether the process of acquisition requires contact with the three dimensional object. A contact-type range acquisition system utilizes a probe, having multiple degrees of translational and/or rotational freedom. By recording the physical displacement of the probe as it is drawn across the sample surface, a computer-readable representation of the sample object is made. A non-contact-type range acquisition device can be either a reflective-type or transmissive-type system. There are a variety of reflective systems in use. Some of these reflective systems utilize non-optical incident energy sources such as microwave radar or sonar. Others utilize optical energy. Those non-contact-type systems working by reflected optical energy further contain special instrumentation configured to permit certain measuring techniques to be performed (e.g., imaging radar, triangulation and interferometry).

A preferred range acquisition system is an optical, reflective, non-contact-type scanner. Non-contact-type scanners are preferred because they are inherently nondestructive (i.e., do not damage the sample object), are generally characterized by a higher capture resolution and scan a sample in a relatively short period of time. One, such scanner is the Cyberware Model 15 manufactured by Cyberware, Inc., Monterey, Calif.

Either non-contact-type or contact-type scanners may also include a color camera, that when synchronized with the scanning capabilities, provides a means for capturing, in digital format, a color representation of the sample object. The importance of this further ability to capture not just the shape of the sample object but also its color is discussed below.

In a preferred embodiment, a wax bite is also obtained from a patient. The wax bite enables scanning of the relative positions of the upper and lower dentition in centric occlusion. This is usually accomplished by first placing the lower cast in front of the scanner, with the teeth facing upwards, then placing the wax bite on top of the lower cast, and finally by placing the upper cast on top of the lower cast, with the teeth downwards, resting on the wax bite. A cylindrical scan is then acquired for the lower and upper casts in their relative positions. The scanned data provides a digital model of medium resolution representing an object which is the combination of the patient's arches positioned in the same relative configuration as in the mouth.

The digital model acts as a template guiding the placement of the two individual digital models (one per arch).

More precisely, using software, for example the CyberWare alignment software, each digital arch is in turn aligned to the pair scan. The individual models are then positioned relative to each other corresponding to the arches in the patient's mouth.

The methods of the present invention will rely on manipulating the IDDS at a computer or workstation having a suitable graphical user interface (GUI) and software appropriate for viewing and modifying the images. Specific aspects of the software will be described in detail hereinafter. While the methods will rely on computer manipulation of digital data, the systems of the present invention comprising multiple dental appliances having incrementally differing geometries may be produced by non-computer-aided techniques. For example, plaster casts obtained as described above may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare sets of multiple appliances, generally as described below, using pressure and vacuum molding techniques. While such manual creation of the appliance systems of the present invention will generally be much less preferred, systems so produced will come within the scope of the present invention.

Referring again to FIG. 2, after the IDDS has been obtained, the digital information will be introduced to the computer or other workstation for manipulation. In the preferred approach, individual teeth and other components will be "cut" to permit their individual repositioning or removal from the digital data. After thus "freeing" the components, the user will often follow a prescription or other written specification provided by the treating professional. Alternatively, the user may reposition them based on the visual appearance or using rules and algorithms programmed into the computer. Once the user is satisfied with the final arrangement, the final tooth arrangement as incorporated into a final digital data set (FDDS).

Figure 3:
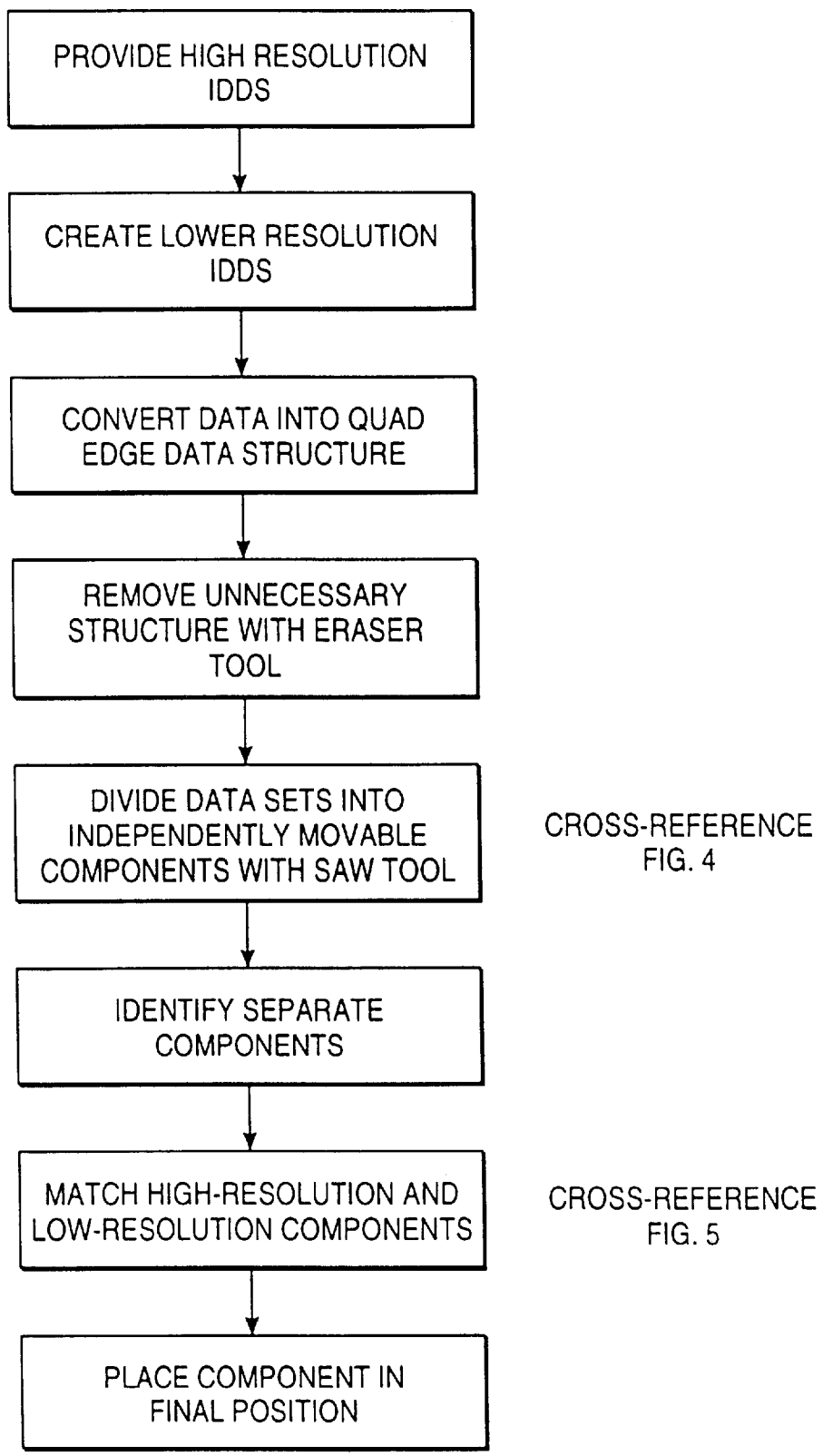
FIG. 3 is a block diagram setting forth the steps for manipulating an initial digital data set representing an initial tooth arrangement to produce a final digital data set corresponding to a desired final tooth arrangement.

Based on both the IDDS and the FDDS, a plurality of intermediate digital data sets (INTDDS's) are generated to correspond to FIG. 3 illustrates a representative technique for manipulating the IDDS to produce the FDDS on the computer. Usually, the data from the digital scanner will be in a high resolution form. In order to reduce the computer time necessary to generate images, a parallel set of digital data set representing the IDDS at a lower resolution will be created. The user will manipulate the lower resolution images while the computer will update the high resolution data set as necessary. The user can also view/manipulate the high resolution model if the extra detail provided in that model is useful. The IDDS will also be converted into a quad edge data structure if not already present in that form. A quad edge data structure is a standard topological data structure defined in *Primitives for the Manipulation of General Subdivisions and the Computation of Voronoi Diagrams*, ACM Transactions of Graphics, Vol. 4, No. 2, April 1985, pp. 74–123. Other topological data structures, such as the winged-edge data structure, could also be used.

As an initial step, while viewing the three-dimensional image of the patient's jaw, including the teeth, gingivae, and other oral tissue, the user will usually delete structure which is unnecessary for image manipulation and/or final production of an appliance. These unwanted sections of the model may be removed using an eraser tool to perform a solid modeling subtraction. The tool is represented by a graphic box. The volume to be erased (the dimensions, position, and orientation of the box) are set by the user employing the GUT. Typically, unwanted sections would include extraneous gum area and the base of the originally scanned cast. Another application for this tool is to stimulate the extraction of teeth and the "shaving down" of tooth surfaces. This is necessary when additional space is needed in the jaw for the final positioning of a tooth to be moved. The treating professional may choose to determine which teeth will be shaved and/or which teeth will be extracted. Shaving allows the patient to maintain their teeth when only a small amount of space is needed. Typically, extraction and shaving, of course, will be utilized in the treatment planning only when the actual patient teeth are to be extracted and/or shaved prior to initiating repositioning according to the methods of the present invention.

Removing unwanted and/or unnecessary sections of the model increases data processing speed and enhances the visual display. Unnecessary sections include those not needed for creation of the tooth repositioning appliance. The removal of these unwanted sections reduces the complexity and size of the digital data set, thus accelerating manipulations of the data set and other operations.

After the user positions and sizes the eraser tool and instructs the software to erase the unwanted section, all triangles within the box set by the user will be removed and the border triangles are modified to leave a smooth, linear border. The software deletes all of the triangles within the box and clips all triangles which cross the border of the box. This requires generating new vertices on the border of the box. The holes created in the model at the faces of the box are re-triangulated and closed using the newly created vertices.

The saw tool is used to define the individual teeth (or possibly groups of teeth) to be moved. The tool separates the scanned image into individual graphic components enabling the software to move the tooth or other component images independent of remaining portions of the model. In one embodiment, the saw tool defines a path for cutting the graphic image by using two cubic B-spline curves lying in space, possibly constrained to parallel planes, either open or closed. A set of lines connects the two curves and shows the user the general cutting path The user may edit the control points on the cubic B-splines, the thickness of the saw cut, and the number of erasers used, as described below.

In an alternate preferred embodiment, the teeth are separated by using the saw as a "coring" device, cutting the tooth from above with vertical saw cuts. The crown of the tooth, as well as the gingivae-tissue immediately below the crown are separated from the rest of the geometry, and treated as an individual unit, referred to as a tooth. When this model is moved, the gingivae tissue moves relative to the crown, creating a first order approximation of the way that the gingivae will reform within a patient's mouth.

Each tooth may also be separated from the original trimmed model. Additionally, a base may be created from the original trimmed model by cutting off the crowns of the teeth. The resulting model is used as a base for moving the teeth. This facilitates the eventual manufacture of a physical mold from the geometric model, as described below.

Thickness: When a cut is used to separate a tooth, the user will usually want the cut to be as thin as possible. However, the user may want to make a thicker cut, for example, when shaving down surrounding teeth, as described above.

Graphically, the cut appears as a curve bounded by the thickness of the cut on one side of the curve.

Figure 4A:
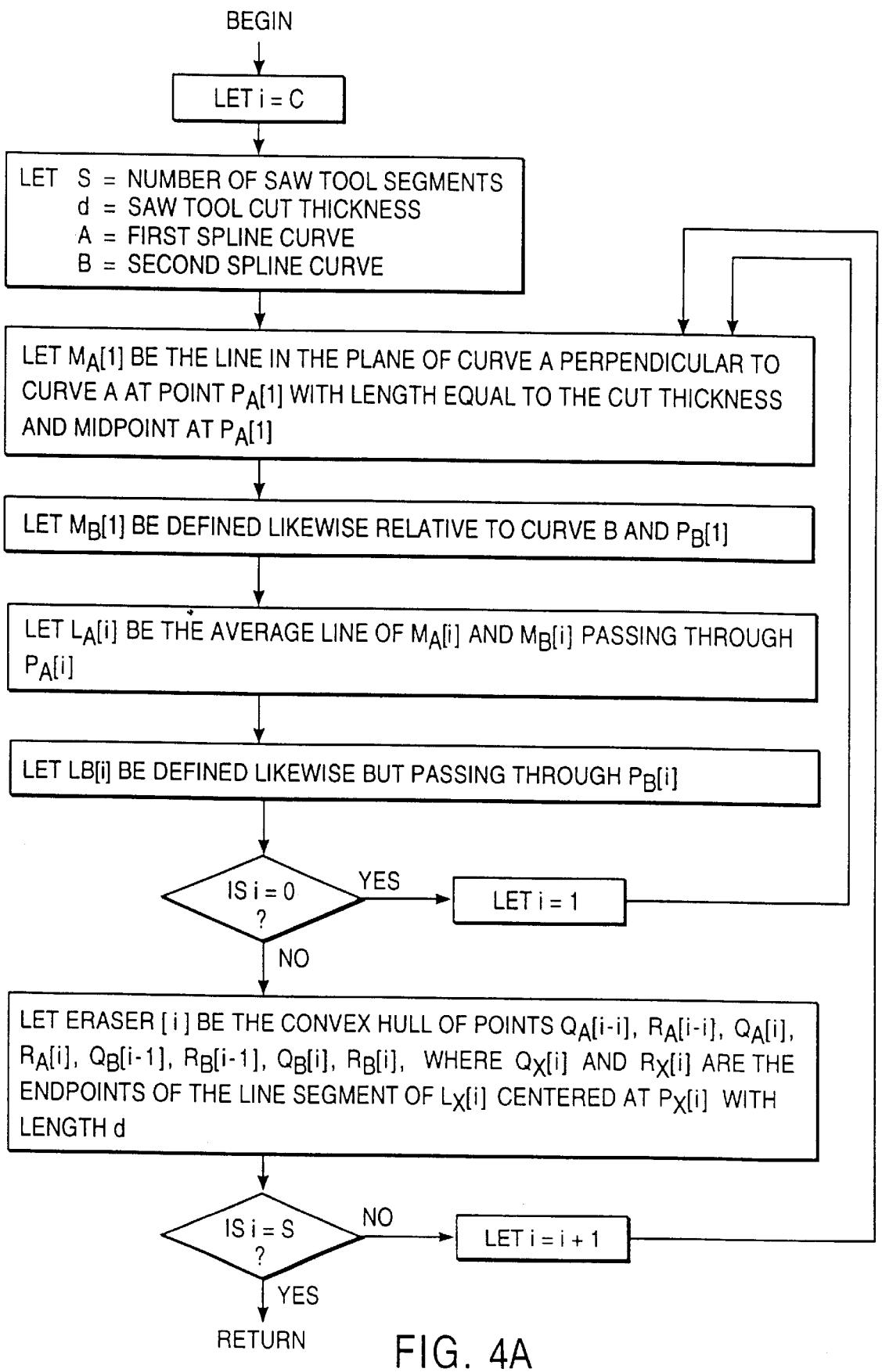
FIG. 4A is a flow chart illustrating an eraser tool for the methods herein.
Figure 4B:
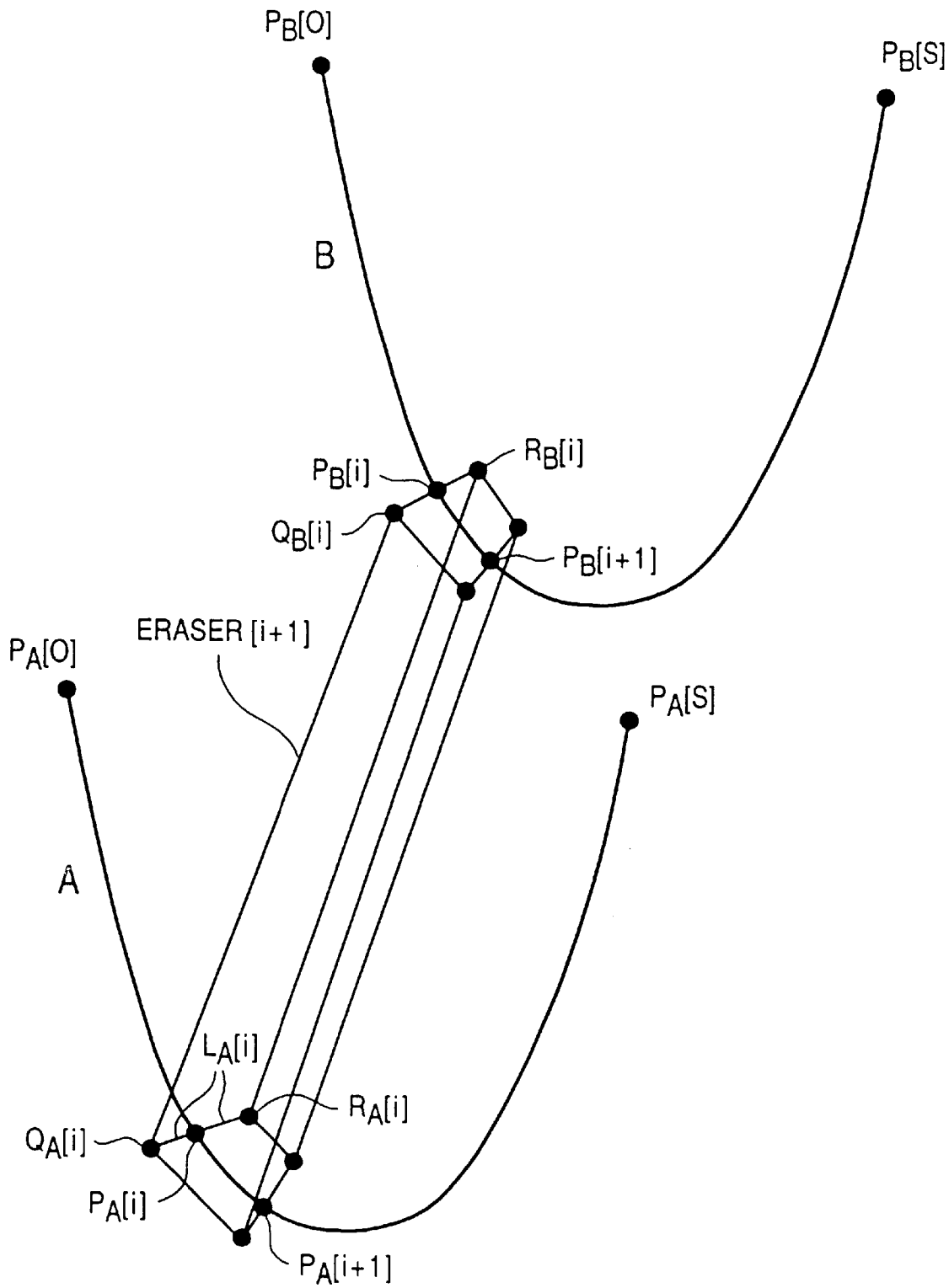
FIG. 4B illustrates the volume of space which is being erased by the program of FIG. 4A.

Number of Erasers: A cut is comprised of multiple eraser boxes arranged next to each other as a piecewise linear approximation of the Saw Tool's curve path. The user chooses the number of erasers, which determines the sophistication of the curve created —the greater the number of segments, the more accurately the cutting will follow the curve. The number of erasers is shown graphically by the number of parallel lines connecting the two cubic B-spline curves. Once a saw cut has been completely specified the user applies the cut to the model. The cut is performed as a sequence of erasings. A preferred algorithm is set forth in FIG. 4A. FIG. 4B shows a single erasing iteration of the cut as described in the algorithm for a open ended B-spline curve. For a vertical cut, the curves are closed with $P_A[O]$ and $P_A[S]$ the same point and $P_B[O]$ and $P_B[S]$ being the same point.

In one embodiment, the software may automatically partition the saw tool into a set of erasers based upon a smoothness measure input by the user. The saw is adaptively subdivided until an error metric measures the deviation from the ideal representation to the approximate representation to be less than a threshold specified by the smoothness setting. The preferred error metric used compares the linear length of the subdivided curve to the arclength of the ideal spline curve. When the difference is greater than a threshold computed from the smoothness setting, a subdivision point is added along the spline curve.

A preview feature may also be provided in the software. The preview feature visually displays a saw cut as the two surfaces that represent opposed sides of the cut. This allows the user to consider the final cut before applying it to the model data set.

After the user has completed all desired cutting operations with the saw tool, multiple graphic solids exist. However, at this point, the software has not determined which triangles of the quad edge data structure belong to which components. The software chooses a random starting point in the data structure and traverses the data structure using adjacency information to find all of the triangles that are attached to each other, identifying an individual component. This process is repeated starting with the triangle whose component is not yet determined. Once the entire data structure is traversed, all components have been identified.

Figure 5:
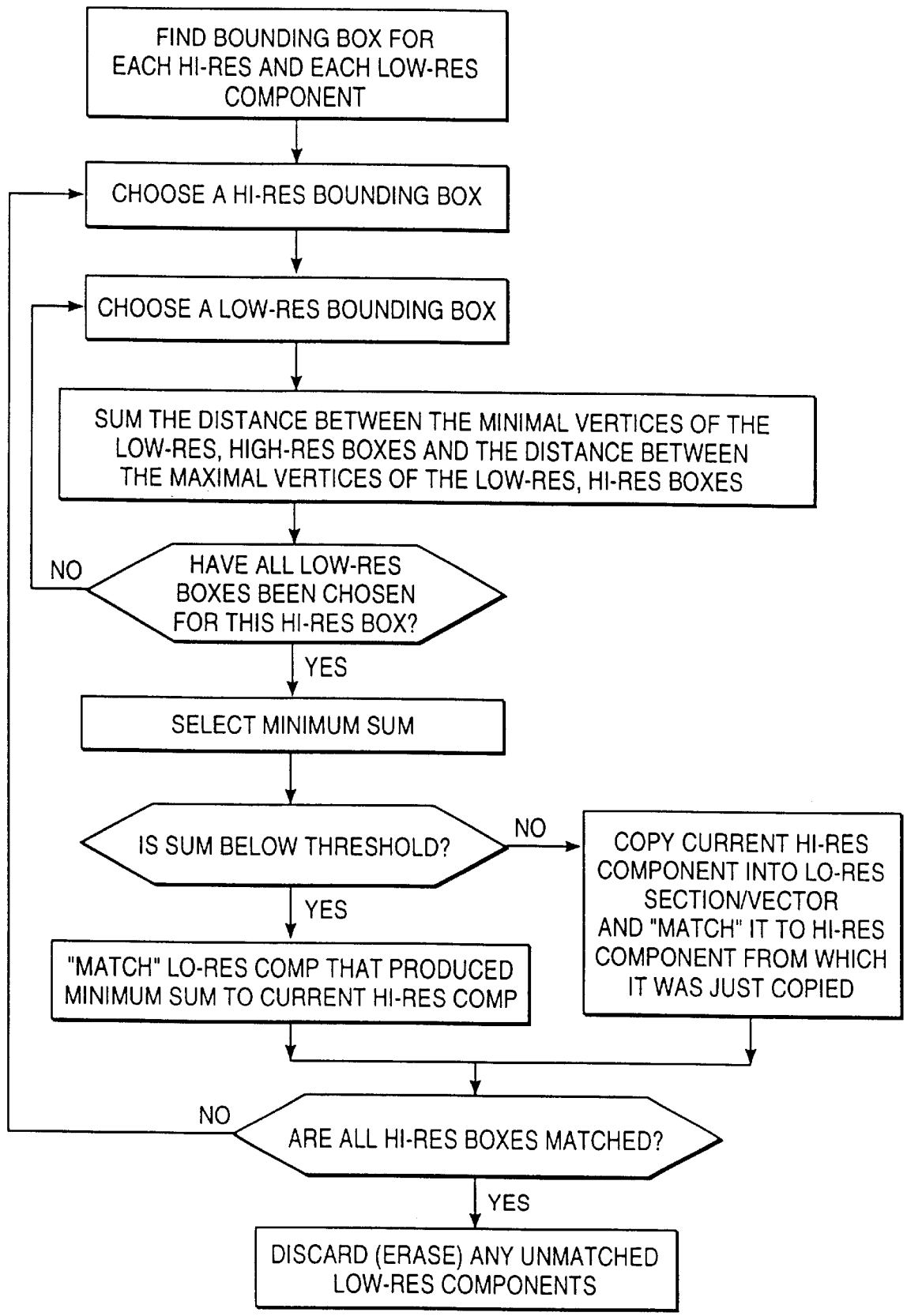
FIG. 5 is a flow chart illustrating a program for matching high-resolution and low-resolution components in the manipulation of data sets of FIG. 3.

To the user, all changes made to the high resolution model appear to occur simultaneously in the low resolution model, and vice versa. However, there is not a one-to-one correlation between the different resolution models. Therefore, the computer "matches" the high resolution and low resolution components as best as it can subject to defined limits. The algorithm is described in FIG. 5.

Cusp detection: In a preferred embodiment, the software provides the ability to detect cusps for a tooth. Cusps are pointed projections on the chewing surface of a tooth. Cusp detection can be performed either before or after the cutting phase has been performed. The algorithm used for cusp detection is composed of two stages: (1) "detection" stage, during which a set of points on the tooth are determined as candidates for cusp locations; and (2) "rejection" stage, during which candidates from the set of points are rejected if they do not satisfy a set of criteria associated with cusps.

Figure 6A:
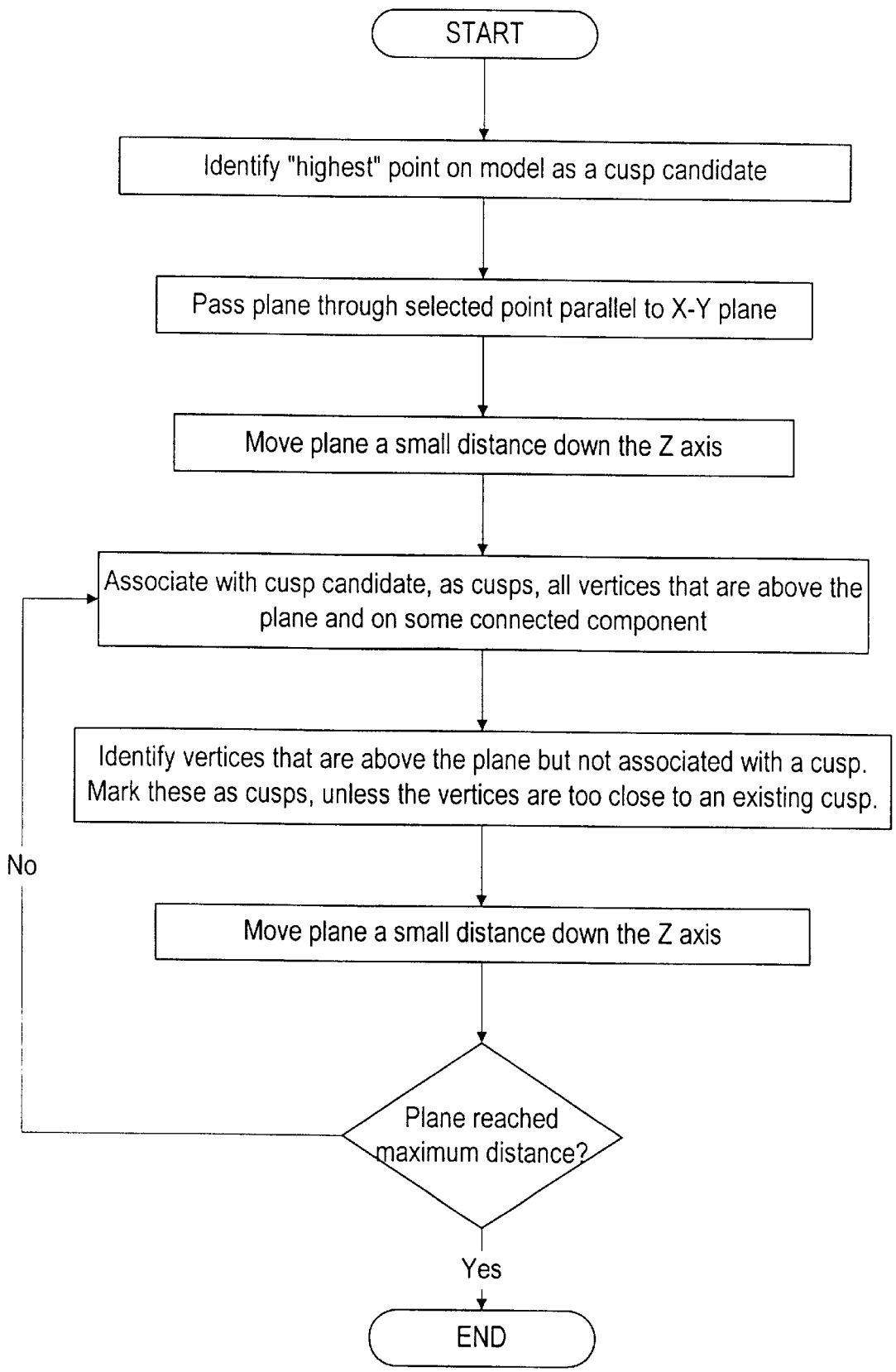
FIG. 6A is a flow chart illustrating a program for performing the "detection" stage of the cusp detection algorithm.

A preferred algorithm for the "detection" stage is set forth in FIG. 6A. In the detection stage, a possible cusp is viewed as an "island" on the surface of the tooth, with the candidate cusp at the highest point on the island. "Highest" is measured with respect to the coordinate system of the model, but could just as easily be measured with respect to the local coordinate system of each tooth if detection is performed after the cutting phase of treatment.

The set of all possible cusps is determined by looking for all local maxima on the tooth model that are within a specified distance of the top of the bounding box of the model. First, the highest point on the model is designated as the first candidate cusp. A plane is passed through this point, perpendicular to the direction along which the height of a point is measured. The plane is then lowered by a small predetermined distance along the Z axis. Next, all vertices connected to the tooth and which are above the plane and on some connected component are associated with the candidate cusp as cusps. This step is also referred to as the "flood fill" step. From each candidate cusp point, outward "flooding" is performed, marking each vertex on the model visited in this matter as "part of" the corresponding candidate cusp. After the flood fill step is complete, every vertex on the model is examined. Any vertex that is above the plane and has not been visited by one of the flood fills is added to the list of candidate cusps. These steps are repeated until the plane is traveled a specified distance.

While this iterative approach can be more time consuming than a local maximum search, the approach described above leads to a shorter list of candidate cusps. Since the plane is lowered a finite distance at each step, very small local maxima that can occur due to noisy data are skipped over.

After the "detection" stage, the cusp detection algorithm proceeds with the "rejection" stage. A preferred algorithm for the "rejection" stage is set forth in FIG. 6B. In this stage, the local geometries around each of cusp candidates are analyzed to determine if they possess "non-cusp-like features." Cusp candidates that exhibit "non-cusp-like features" are removed from the list of cusp candidates.

Figure 6B:
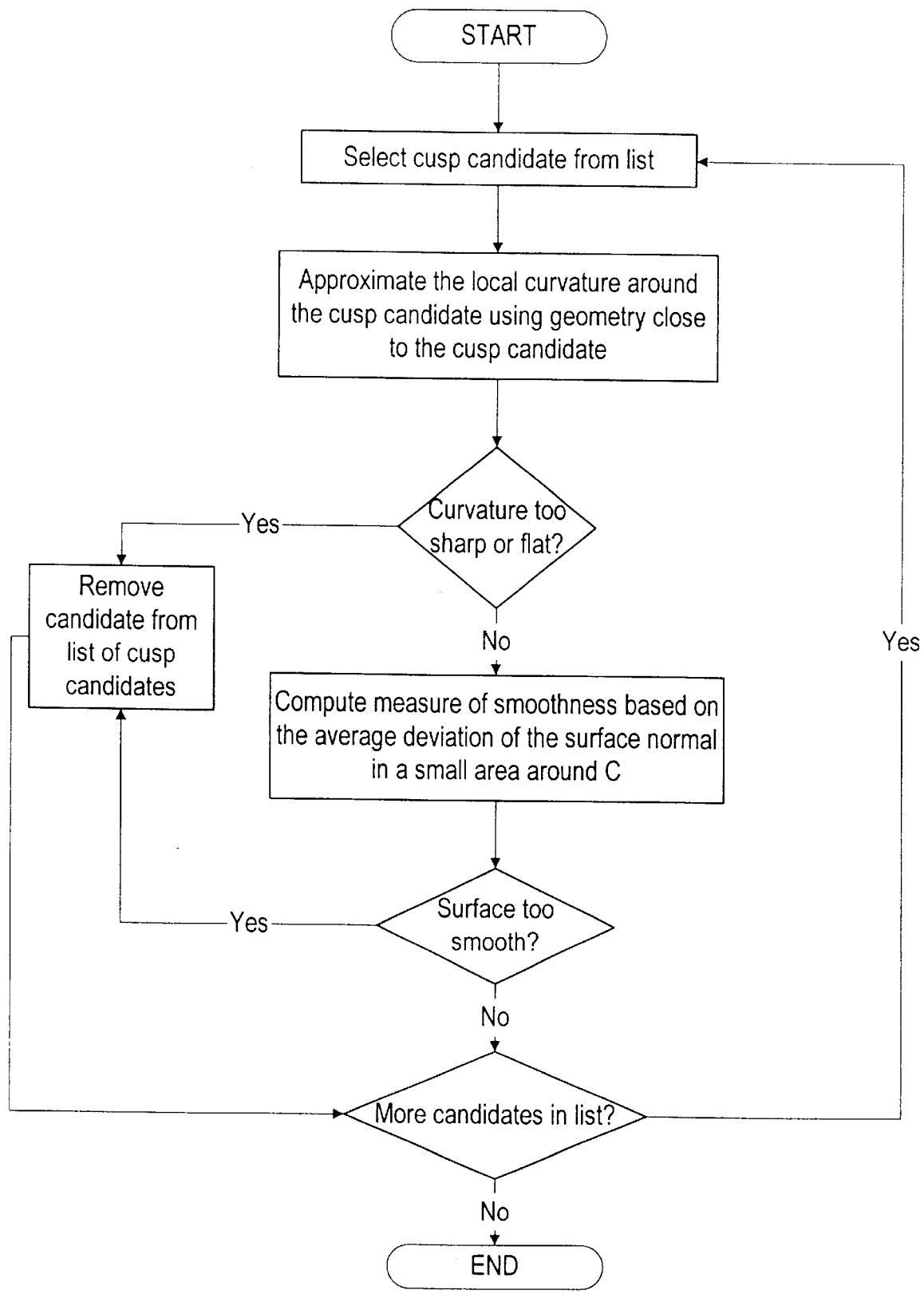
FIG. 6B is a flow chart illustrating a program for performing the "rejection" stage of the cusp detection algorithm.

Various criteria may be used to identify "non-cusp-like features.", According to one test, the local curvature of the surface around the cusp candidate is used to determine whether the candidate possesses non-cusp-like features. As depicted in FIG. 6B, the local curvature of the surface around the cusp candidate is approximated, and then analyzed to determine if it is too large (very pointy surface) or too small (very flat surface), in which case the candidate is removed from the list of cusp candidates. Conservative values are used for the minimum and maximum curvatures values to ensure that genuine cusps are not rejected by mistake.

According to an alternate test, a measure of smoothness is computed based on the average normal in an area around the candidate cusp. If the average normal deviates from the normal at the cusp by more than a specified amount, the candidate cusp is rejected. In a preferred embodiment, the deviation of a normal vector N from the cusp normal CN is approximated by the formula:

$$1-Abs(N*CN),$$

which is zero at no deviation, and 1 when N and CN are perpendicular.

Once the teeth have been separated, the FDDS can be created from the IDDS. The FDDS is created by following the orthodontists prescription, moving the teeth into their final prescription. In one embodiment, the prescription is entered into a computer, which algorithmically computes the final position of the teeth. In alternate embodiments, a user may move the teeth into their final positions by independently manipulating one or more teeth while satisfying the constraints of the prescription it should be appreciated that various combinations of the above described techniques may also be used to arrive at the final teeth position.

The preferred method for creating the FDDS involves moving the teeth in a specified sequence. First, the centers of each of the teeth are aligned to a standard arch. Then, the teeth are rotated until their roots are in the proper vertical position. Next, the teeth are rotated around their vertical axis into the proper orientation. The teeth are then observed from the side, and translated vertically into their proper vertical position. Finally, the two arches are placed together, and the teeth moved slightly to ensure that the upper and lower arches properly mesh together. The meshing of the upper and lower arches together is visualized using the collision detection algorithm to highlight the contacting points of the teeth in red.

Figure 7:
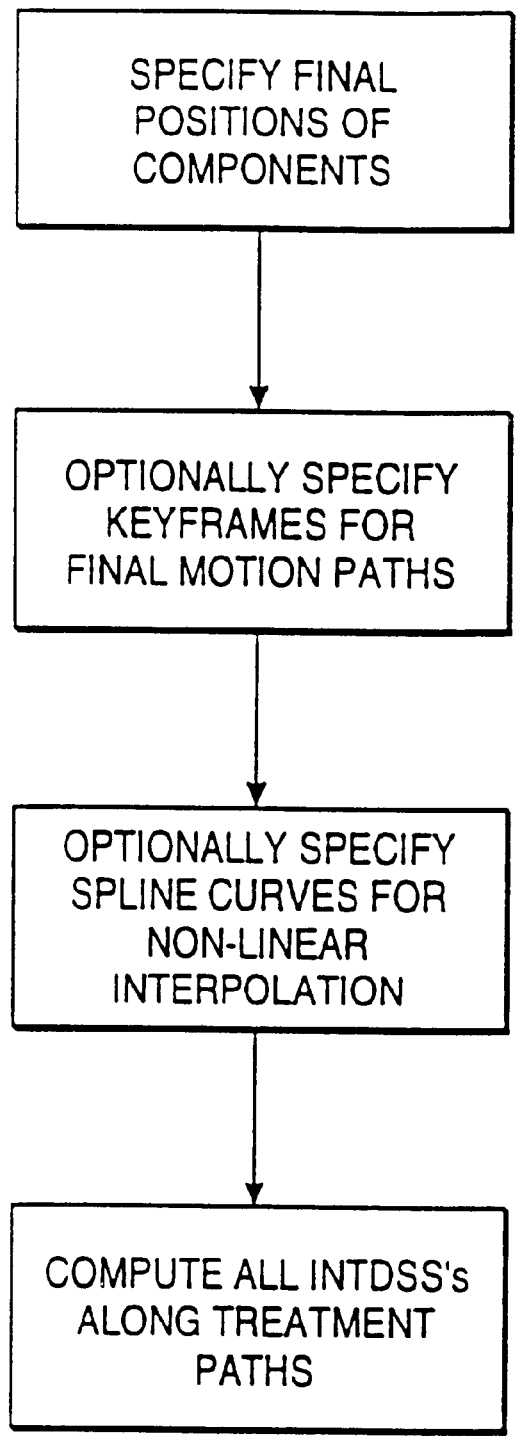
FIG. 7 illustrates the method for generating multiple intermediate digital data sets which are used for producing the adjustment appliances of the present invention.

After the teeth and other components have been placed or is removed so that the final tooth arrangement has been produced, it is necessary to generate a treatment plan, as illustrated in FIG. 7. The treatment plan will ultimately produce the series of INTDDS's and FDDS as described previously. To produce these data sets, it is necessary to, define or map the movement of selected individual teeth from the initial position to the final position over a series of successive steps. In addition, it may be necessary to add other features to the data sets in order to produce desired features in the treatment appliances. For example, it may be desirable to add wax patches to the image in order to define cavities or recesses for particular purposes. For example, it may be desirable to maintain a space between the appliance and particular regions of the teeth or jaw in order to reduce soreness of the gums, avoid periodontal problems, allow for a cap, and the like. Additionally, it will often be necessary to provide a receptacle or aperture intended to accommodate an anchor which is to be placed on a tooth in order to permit the tooth to be manipulated in a manner that requires the anchor, e.g. lifted relative to the jaw.

Some methods for manufacturing the tooth repositioning appliances require that the separate, repositioned teeth and other components be unified into a single continuous structure in order to permit manufacturing. In these instances, "wax patches" are used to attach otherwise disconnected components of the INTDDS's. These patches are added to the data set underneath the teeth and above the gum so that they do not effect the geometry of the tooth repositioning appliances. The application software provides for a variety of wax patches to be added to the model, including boxes and spheres with adjustable dimensions. The wax patches that are added are treated by the software as additional pieces of geometry, identical to all other geometries. Thus, the wax patches can be repositioned during the treatment path as well as the teeth and other components. The preferred method of separating the teeth using vertical coring, as described above, removes the need for most of these "wax patches".

In the manufacturing process, which relies on generation of positive models to produce the repositioning appliance, adding a wax patch to the graphic model will generate a positive mold that has the same added wax patch geometry. Because the mold is a positive of the teeth and the appliance is a negative of the teeth, when the appliance is formed over the mold, the appliance will also form around the wax patch that has been added to the mold. When placed in the patient's mouth, the appliance will thus allow for a space between the inner cavity surface of the appliance and the patient's teeth or gums. Additionally, the wax patch may be used to form a recess or aperture within the appliance which engages an anchor placed on the teeth in order to move the tooth in directions which could not otherwise be accomplished.

In addition to such wax patches, an individual component, usually a tooth, can be scaled to a smaller or larger size which will result in a manufactured appliance having a tighter or looser fit, respectively.

Treatment planning is extremely flexible in defining the movement of teeth and other components. The user may change the number of treatment stages, as well as individually control the path and speed of components.

Number of Treatment Stages: The user can change the number of desired treatment stages from the initial to the target states of the teeth. Any component that is not moved is assumed to remain stationary, and thus its final position is assumed to be the same as the initial position (likewise for all intermediate positions, unless one or more key frames are defined for that component).

Key frames: The user may also specify "key frames" by selecting an intermediate state and making changes to component position(s). Unless instructed otherwise, the software automatically linearly interpolates between all user-specified positions (including the initial position, all key frame positions, and the target position). For example, if only a final position is defined for a particular component, each subsequent stage after the initial stage will simply show the component an equal linear distance and rotation (specified by a quaternion) closer to the final position. If the user specifies to key frames for that component, it will "move" linearly from the initial position through different stages to the position defined by the first key frame. It will then move, possibly in a different direction, linearly to the position defined by the second key frame. Finally, it will move, possibly in yet a different direction, linearly to the target position.

The user can also specify non-linear interpolation between the key frames. A spline curve is used to specify the interpolating function in a conventional manner.

These operations may be done independently to each component, is so that a key frame for one component will not affect another component, unless the other component is also moved by the user in that key frame. One component may accelerate along a curve between stages 3 and 8, while another moves linearly from stage 1 to 5, and then changes direction suddenly and slows down along a linear path to stage 10. This flexibility allows a great deal of freedom in planning a patient's treatment.

In one embodiment, the software automatically determines the treatment path, based upon the IDDS and the FDDS. This is usually accomplished using a path scheduling algorithm which determines the rate at which each component, i.e. a tooth, moves along a straight path from the initial position to the final position. The path scheduling algorithm used by the present invention determines the treatment path while avoiding "round-tripping" which is the term used by orthodontists referring to moving a tooth along a distance greater than absolutely necessary to straighten the teeth. Such motion is highly undesirable, and has potential negative side effects on the patient. In order to avoid "round-tripping", the path scheduling algorithm schedules or stages the movements of all the teeth by constraining them to the shortest straight-line path between the initial and final position, while avoiding all interferences between separate teeth.

The path scheduling algorithm utilizes a randomized search technique to find an unobstructed path through a configuration space which describes possible treatment plans. A preferred embodiment of the algorithm for scheduling motion between two user defined global keyframes is described below. Scheduling over a time interval which includes intermediate keyframes is accomplished by dividing the time interval into subintervals which do not include intermediate keyframes, scheduling each of these intervals independently, and then concatenating the resulting schedules.

Figure 8A:
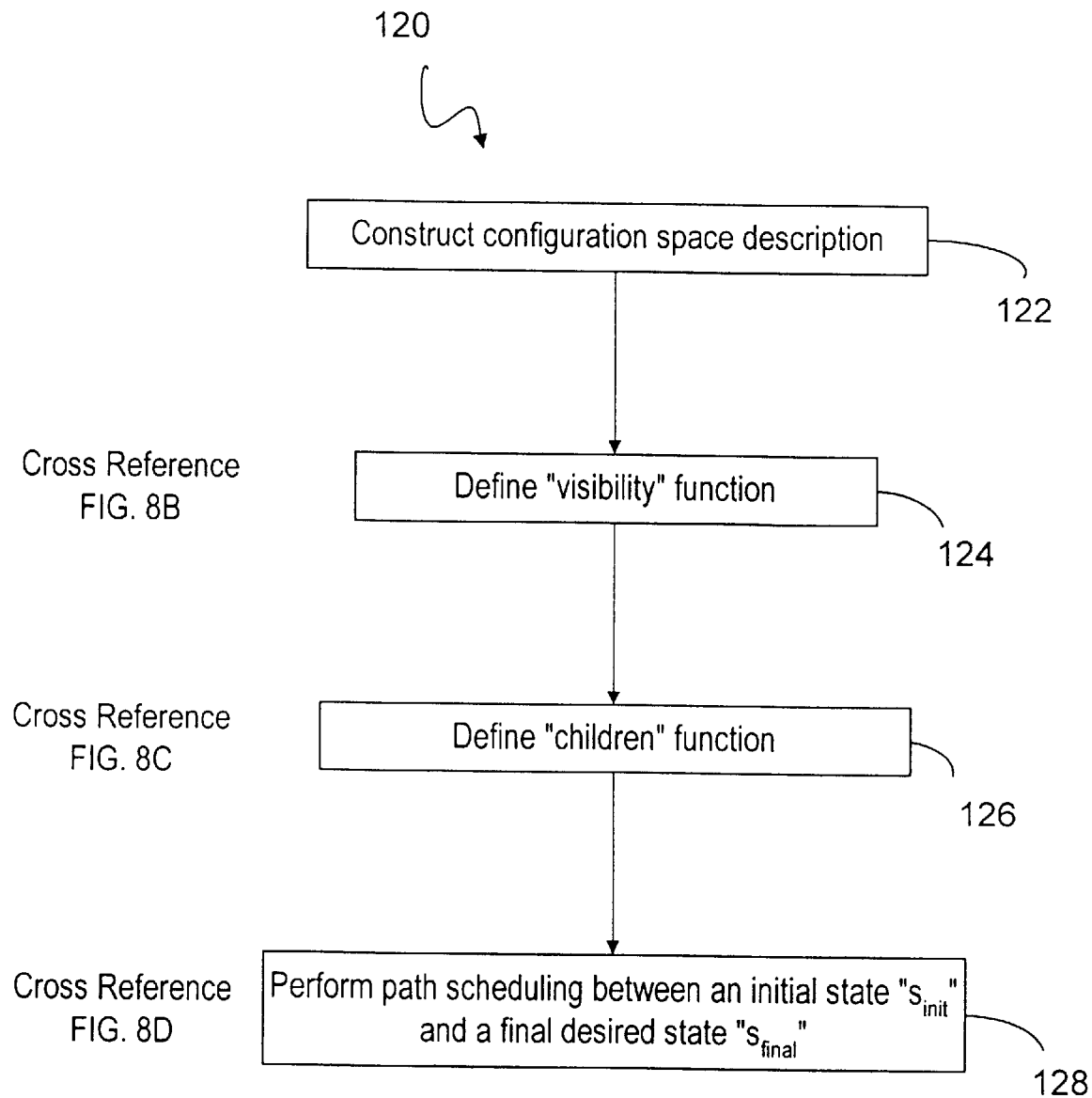
FIG. 8A is a flow chart illustrating the steps performed by the path scheduling algorithm.

Flow chart 120 in FIG. 8A depicts a simplified path scheduling algorithm according to one embodiment of the present invention. in FIG. 8A, first step 122 involves construction of the "configuration space" description. A "configuration" in this context, refers to a given set of positions of all the teeth being considered for movement. Each of these positions may be described in multiple ways. In a preferred embodiment of the present invention, the positions are described by one affine transformation to specify change in location and one rotational transformation to specify the change in orientation of a tooth from its initial position to its final position. The intermediate positions of each tooth are described by a pair of numbers which specify how far to interpolate the location and orientation between the two endpoints. A "configuration" thus consists of two numbers for each tooth being moved, and the "configuration space" refers to the space of all such number pairs. Thus, the configuration space is a Cartesian space, any location in which can be interpreted as specifying the positions of all teeth.

The affine transformation describing the movement of each tooth from its starting position to its ending position is decomposed into translational and rotational components; these transformations are independently interpolated with scalar parameters which are considered two dimensions of the configuration space. The entire configuration space thus consists of two dimensions per moved tooth, all of which are treated equivalently during the subsequent search.

The configuration space is made of "free space" and "obstructed space." "Free" configurations are those which represent valid, physically realizable positions of teeth, while "obstructed" configurations are those which do not. To determine whether a configuration is free or obstructed, a model is created for the positions of the teeth which the configuration describes. A collision detection algorithm is then applied to determine if any of the geometries describing the tooth surfaces intersect. If there are no obstructions, the space is considered free; otherwise it is obstructed. The collision detect algorithm is discussed below in more detail.

Figure 8B:
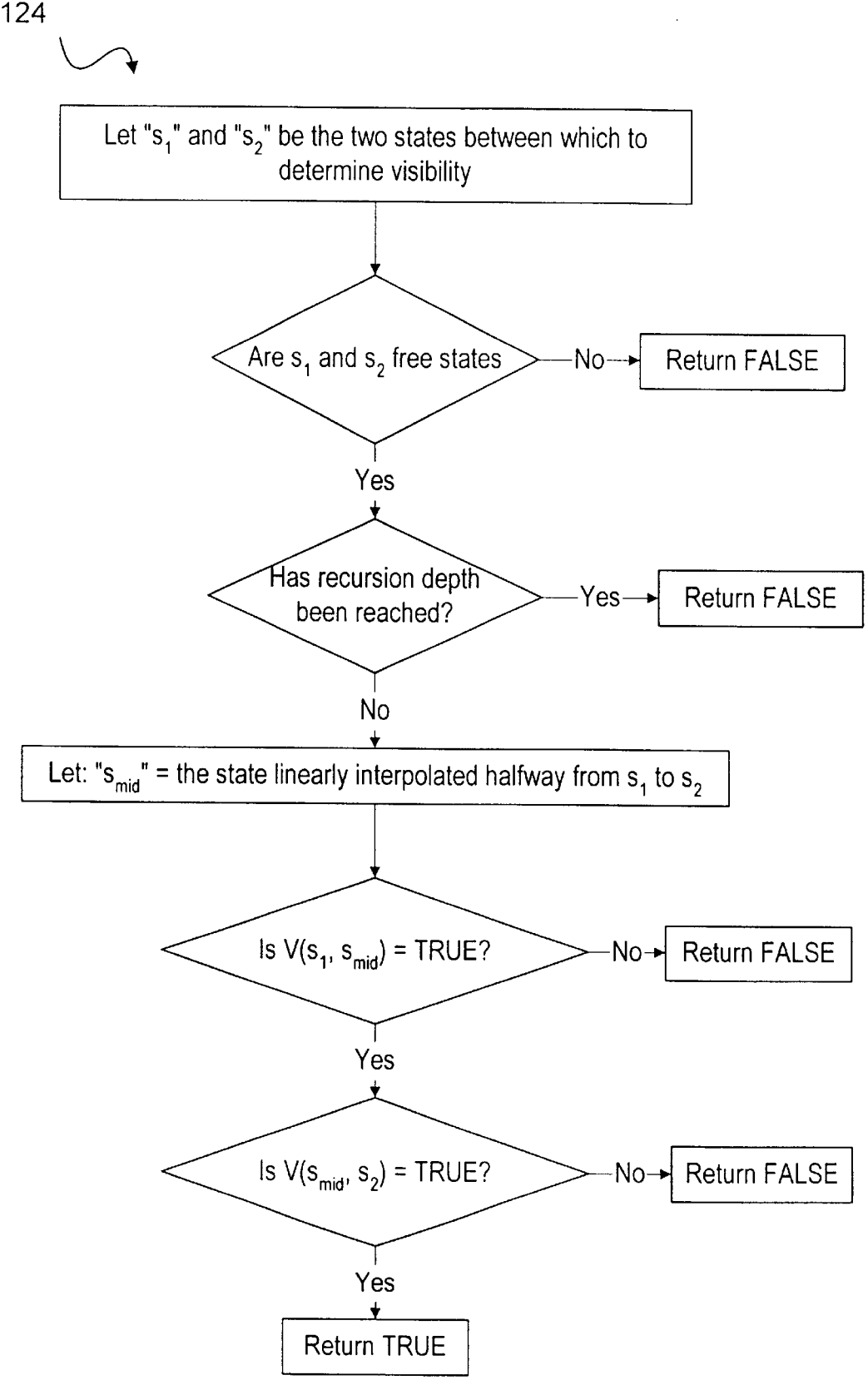
FIG. 8B is a flow chart illustrating the steps for performing the "visibility" function according to one embodiment of the present invention.

At step 124, a "visibility" function $V(s_i, s_2)$ is defined which takes two vectors in the configuration space, "$s_1$" and "$s_2$", as input and returns a true or false boolean value. The visibility function returns a true value if and only if a straight line path connecting $s_1$ and $s_2$ passes entirely through a free and unobstructed region of the configuration space. A preferred algorithm for the visibility function is set forth in FIG. 8B. The visibility function is approximately computed by testing the teeth model for interferences at discretely sampled points along the line $s_1$–$s_2$. Techniques, such as early termination on failure or choosing the order of sample points by recursively subdividing the interval to be tested, may be used to increase the efficiency of the visibility function.

Figure 8C:
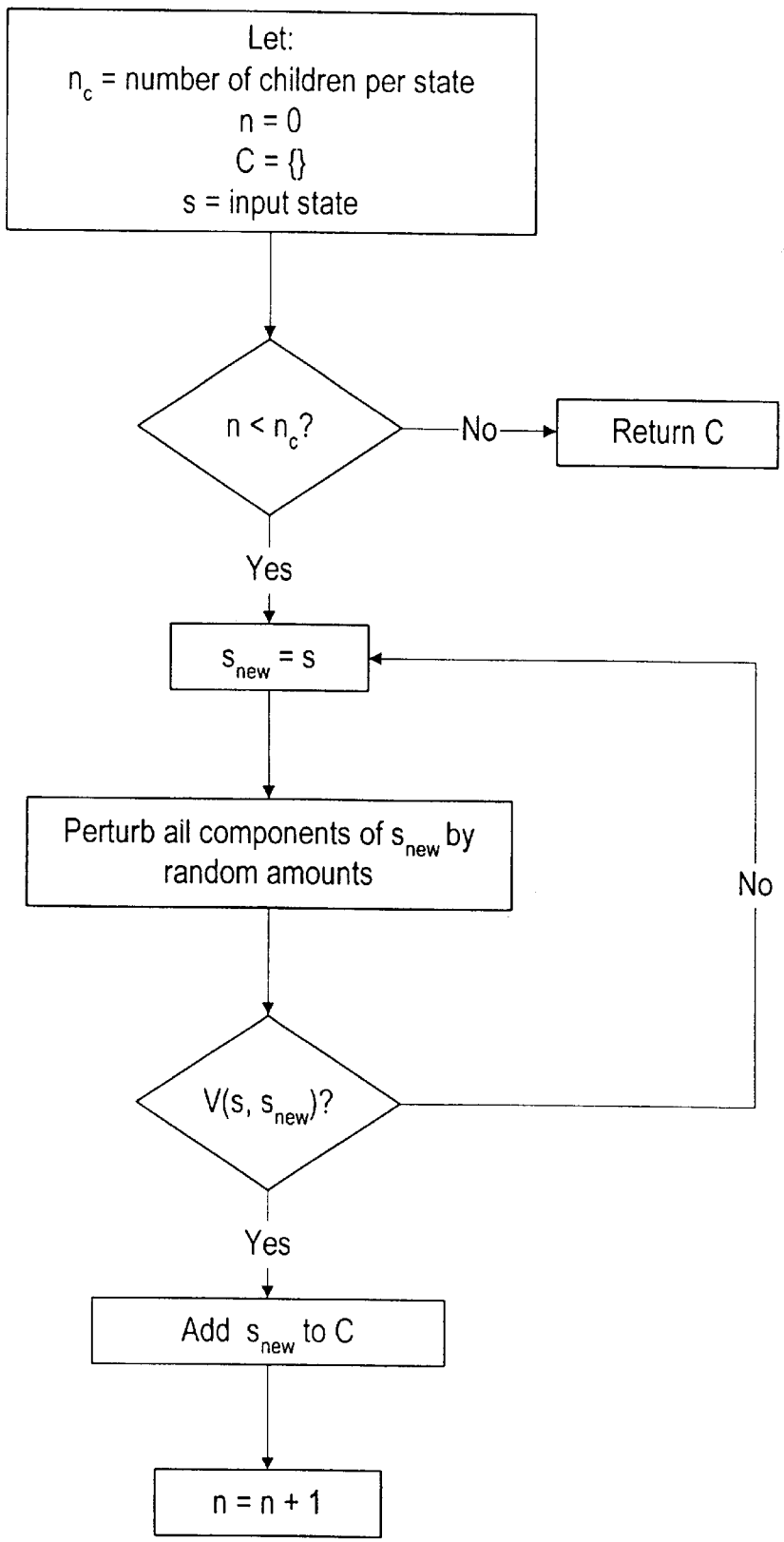
FIG. 8C is a flow chart illustrating the steps for performing the "children" function according to one embodiment of the present invention.

At step 126 of FIG. 8A, a "children" function C(s) is defined whose input parameter, "s", is a vector in the configuration space and, which returns a set of vectors, "$s_C$" in the configuration space. FIG. 8C depicts a simplified flow chart illustrating the steps followed for computing children function C(s). Each vector within set $s_C$ satisfies the property that $V(s, s_C)$ is true and that each of its components are greater than or equal to the corresponding component of "s." This implies that any state represented by such a vector is reachable from "s" without encountering any interferences and without performing any motion which is not in the direction prescribed by treatment. Each vector of set "$s_C$" is created by perturbing each component of "s" by some random, positive amount. The visibility function $V(s, s_C)$ is then computed and "s" added to the set "$s_C$" if the visibility function returns a true boolean value. Additionally, for each such vector generated, a pointer to its parent "s" is recorded for later use.

Figure 8D:
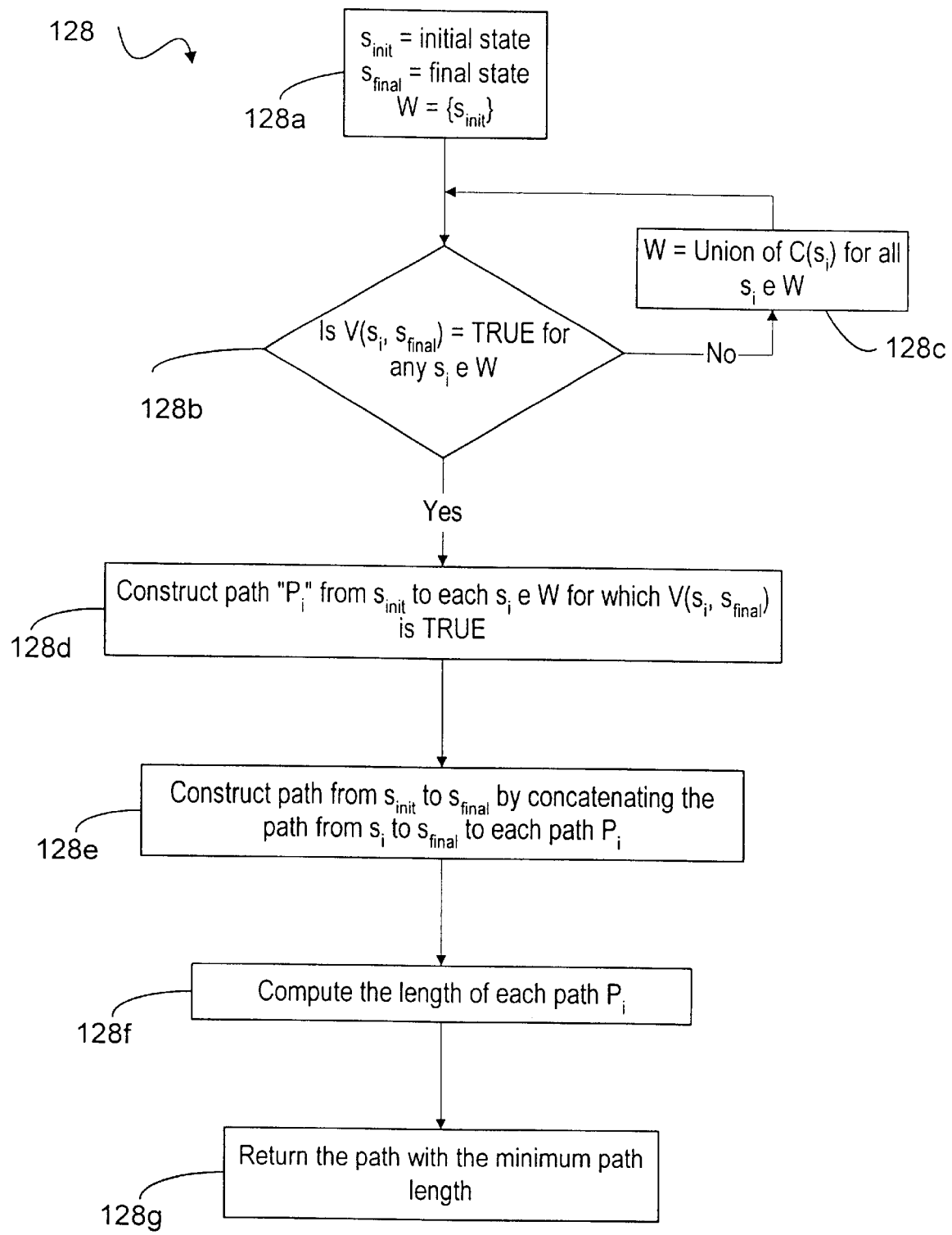
FIG. 8D is a flow chart illustrating the steps for performing path scheduling step 128 of FIG. 8A.

After the configuration space has been defined, at step 128, path scheduling is performed between an initial state "$s_{init}$" and a final state "$s_{final}$." FIG. 8D depicts a preferred flow chart for performing step 128 depicted in FIG. 8A. As illustrated in FIG. 8D, at step 128a, a set of states "W" is defined to initially contain only the initial state $s_{init}$. Next, at step 128b, the visibility function is invoked to determine if $V(s, s_{final})$ is true for at least one state $s_i$ in W. If the visibility function returns a false boolean value, at step 128c, the set of states "W" is replaced with the union of $C(s_i)$ for all $s_i$ in W. Steps 128b and 128c are repeated until $V(s_i, s_{final})$ returns a true boolean value for any $s_i$ belonging to W.

At step 128d, for each $s_i$ for which $V(s_i, s_{final})$ is true, an unobstructed path $P_i$ is constructed from $s_i$ to $s_{init}$ by following the parent pointers back to $s_{init}$. At step 128e, the path from $s_{init}$ to $s_{final}$ is then constructed by concatenating the paths $P_i$ with the final step from $s_i$ to $s_{final}$. If there are multiple paths from $s_{init}$ to $s_{final}$, the total length of each path is computed at step 128f. Finally, at step 128g, the path with the shortest length is then chosen as the final path. The length of the chosen path corresponds to the total time and stages required for a treatment plan.

The resulting final path consists of a series of vectors, each of which represents a group of values of the interpolation parameters of the translational and rotational components of the transformations of the moving teeth. Taken together, these constitute a schedule of tooth movement which avoids tooth-to-tooth interferences.

Collision detect algorithm: The collision or interference detection algorithm employed by the present invention is based on the algorithm described in SIGGRAPH article, Stefan Gottschalk et al. (1996): "*OBBTree: A Hierarchical Structure for Rapid Interference Detection.*" The contents of the SIGGRAPH article are herein incorporated by reference.

The algorithm is centered around a recursive subdivision of the space occupied by an object, which is organized in a binary-tree like fashion. Triangles are used to represent the teeth in the DDS. Each node of the tree is referred to as an oriented bounding box (OBB) and contains a subset of triangles appearing in the node's parent. The children of a parent node contain between them all of the triangle data stored in the parent node.

Figure 9A:
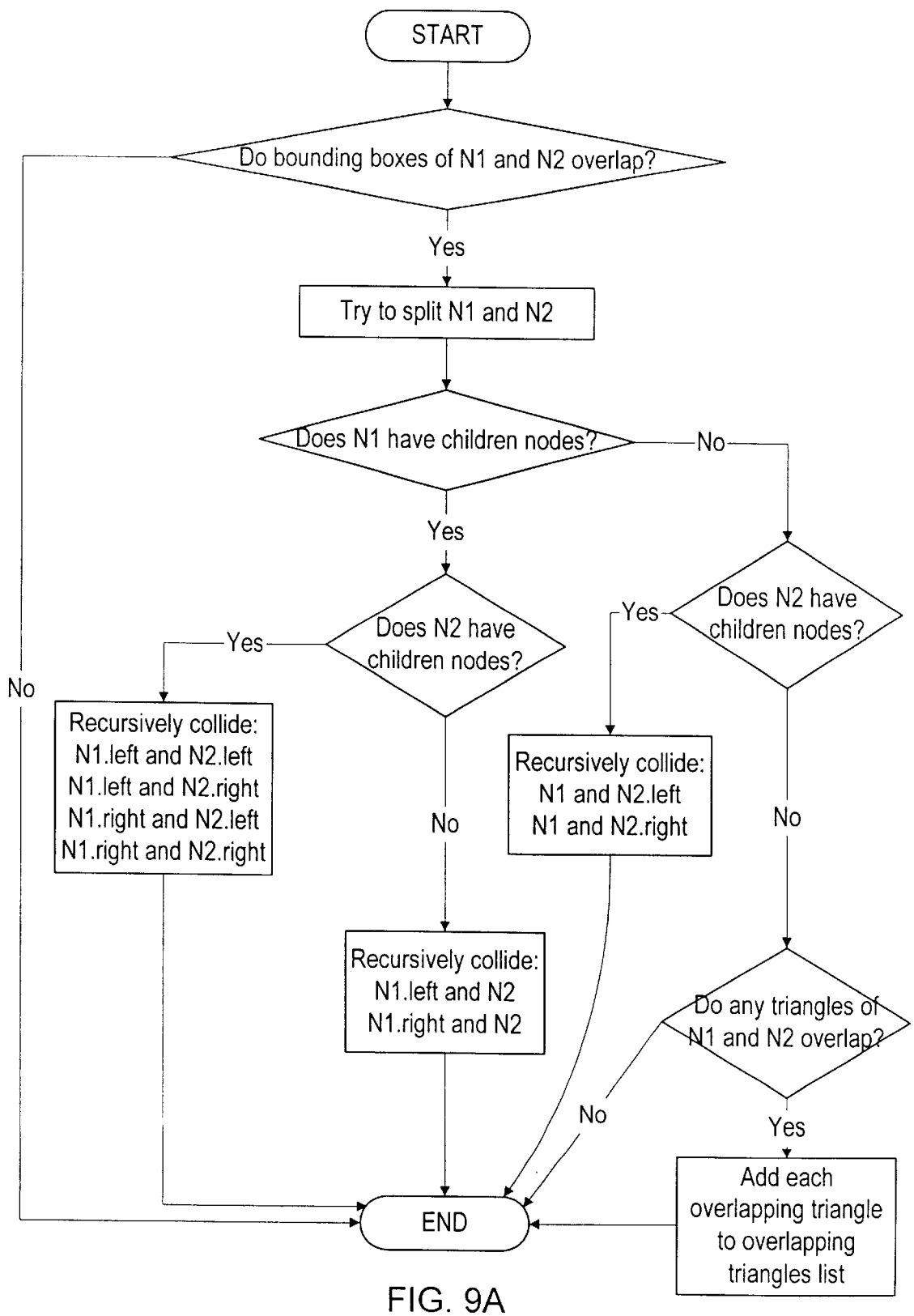
FIG. 9A is a flow chart illustrating the steps for performing recursive collision testing during collision detection.

The bounding box of a node is oriented so it tightly fits around all of the triangles in that node. Leaf nodes in the tree ideally contain a single triangle, but can possibly contain more than one triangle. Detecting collisions between two objects involves determining if the OBB trees of the objects intersect. FIG. 9A sets forth a flow chart depicting a simplified version of a recursive collision test to check if a node "N1" from a first object intersects with node "N2" of a second object. If the OBBs of the root nodes of the trees overlap, the root's children are checked for overlap. The algorithm proceeds in a recursive fashion until the leaf nodes are reached. At this point, a robust triangle intersection routine is used to determine if the triangles at the leaves are involved in a collision.

Figure 9B:
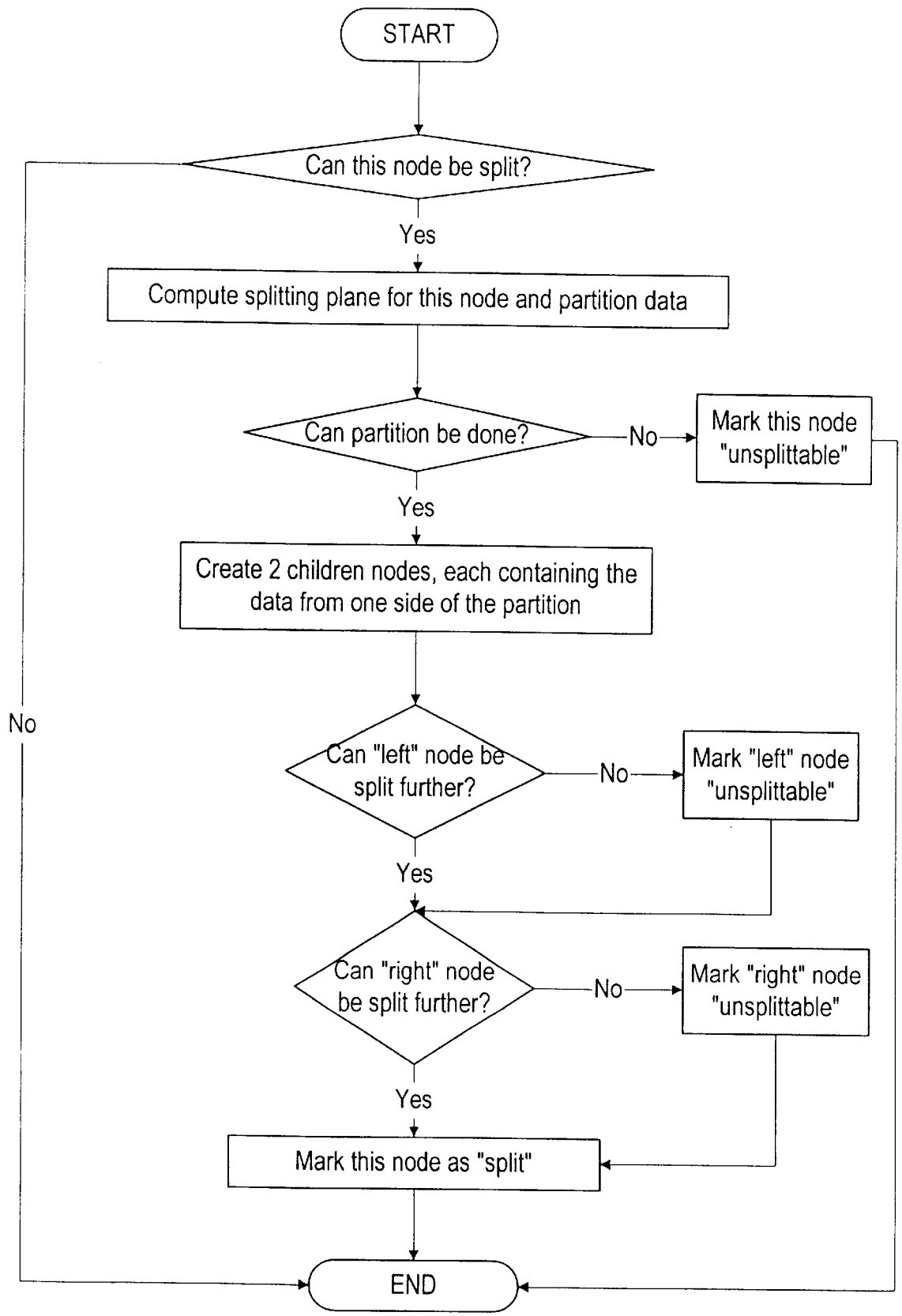
FIG. 9B is a flow chart illustrating node splitting performed during collision detection according to an embodiment of the present invention.

The present invention provides several enhancements to the collision detection algorithm described in the SIGGRAPH article. In one embodiment, the present invention provides a unique method of building OBB trees in a lazy fashion to save memory and time. This approach stems from the observation that there are parts of the model which will never be involved in a collision, and consequently the OBB tree for such parts of the model need not be computed. The OBB trees are expanded by splitting the internal nodes of the tree as necessary during the recursive collision determination algorithm, as depicted in FIG. 9B.

Figure 9C:
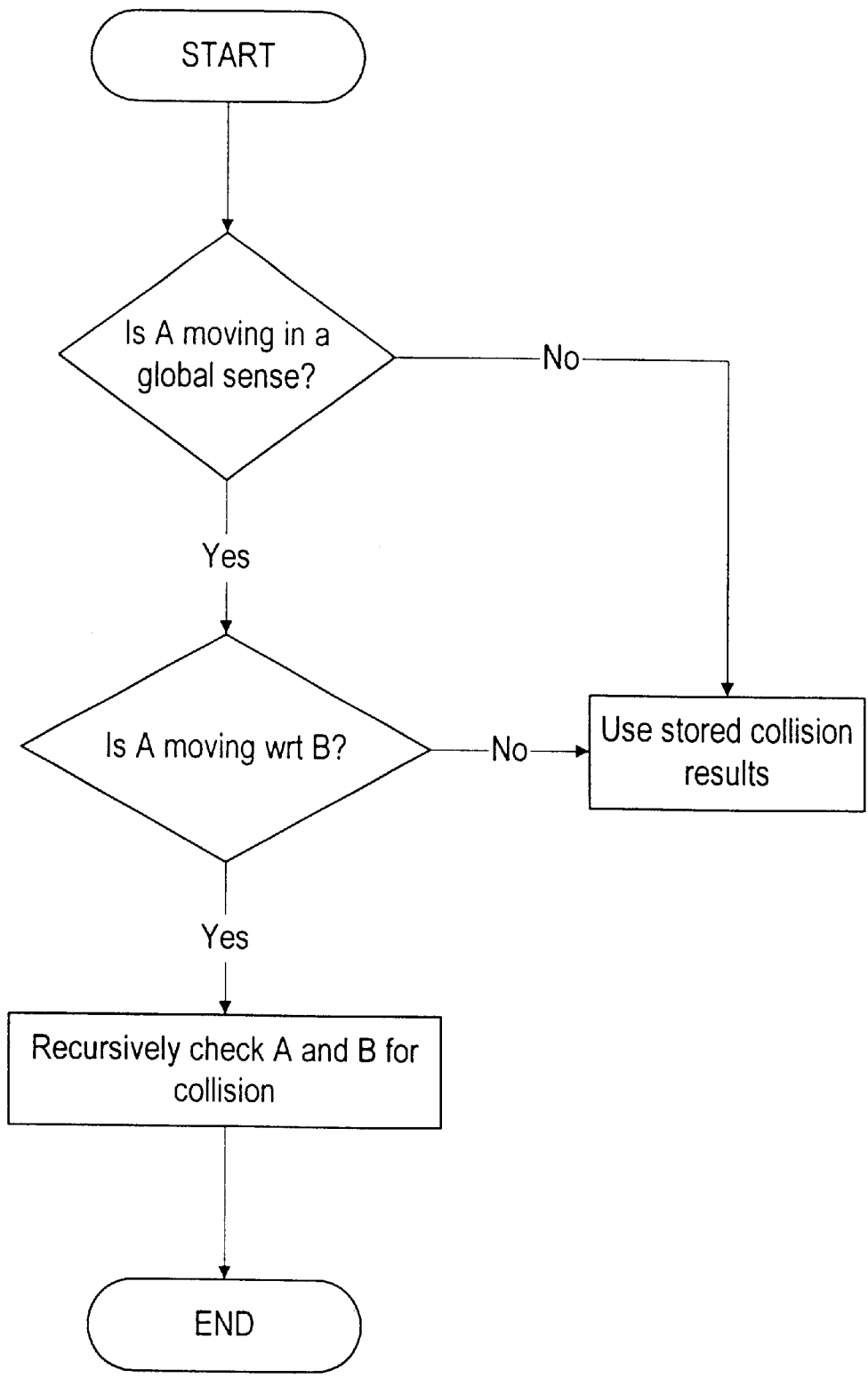
FIG. 9C is a flow chart illustrating steps for providing additional motion information to the collision detection process.

In another embodiment of the present invention, the triangles in the model which are not required for collision data may also be specifically excluded from consideration when building an OBB tree. As depicted in FIG. 9C, additional information is provided to the collision algorithm to specify objects in motion. Motion may be viewed at two levels. Objects may be conceptualized as "moving" in a global sense, or they may be conceptualized as "moving" relative to other objects. The additional information improves the time taken for the collision detection by avoiding recomputation of collision information between objects which are at rest relative to each other since the state of the collision between such objects does not change.

The software of the present invention may also incorporate and the user may at any point use a "movie" feature to automatically animate the movement from initial to target states. This is helpful for visualizing overall component movement throughout the treatment process.

Above it was described that the preferred user interface for component identification is a three dimensional interactive GUI. A three-dimensional GUI is also preferred for component manipulation. Such an interface provides the treating professional or user with instant and visual interaction with the digital model components. It is preferred over interfaces that permit only simple low-level commands for directing the computer to manipulate a particular segment. In other words, a GUI adapted for manipulation Is preferred over an interface that accepts directives, for example, only of the sort: "translate this component by 0.1 mm to the right." Such low-level commands are useful for fine-tuning, but, if they were the sole interface, the processes of component manipulation would become a tiresome and time-consuming interaction.

Before or during the manipulation process, one or more tooth components may be augmented with template models of tooth roots. Manipulation of a tooth model augmented with a root template is useful, for example, in situations where impacting of teeth below the gumline is a concern. These template models could, for example, comprise a digitized representation of the patient's teeth x-rays.

The software also allows for adding annotations to the datasets which can comprise text and/or the sequence number of the apparatus. The annotation is added as recessed text (i.e. it is 3-D geometry), so that it will appear on the printed positive model. If the annotation can be placed on a part of the mouth that will be covered by a repositioning appliance, but is unimportant for the tooth motion, the annotation may appear on the delivered repositioning appliance(s).

The above-described component identification and component manipulation software is designed to operate at a sophistication commensurate with the operator's training level. For example, the component manipulation software can assist a computer operator, lacking orthodontic training, by providing feedback regarding permissible and forbidden manipulations of the teeth. On the other hand, an orthodontist, having greater skill in intraoral physiology and teeth-moving dynamics, can simply use the component identification and manipulation software as a tool and disable or otherwise ignore the advice.

Figure 10:
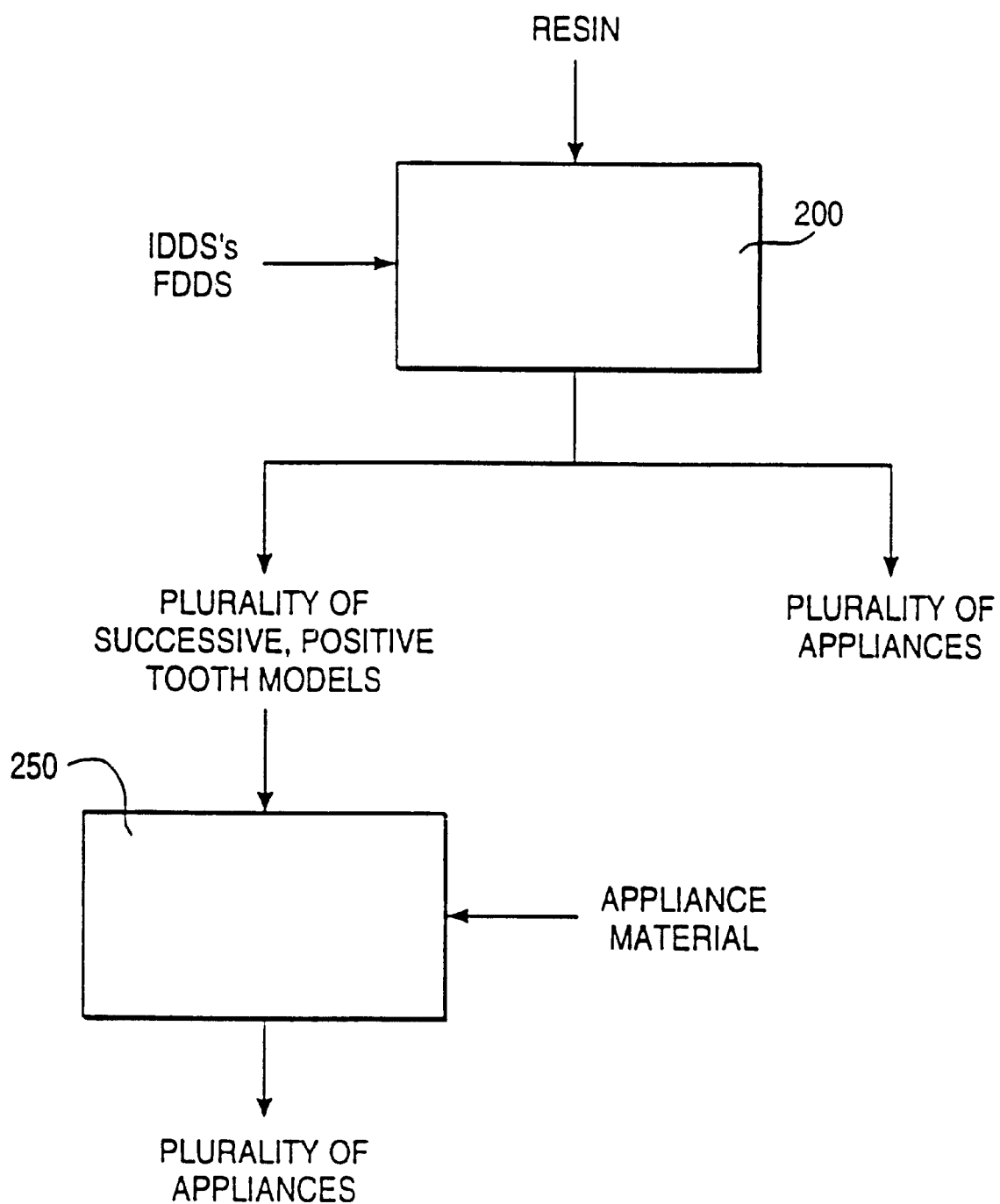
FIG. 10 illustrates alternative processes for producing a plurality of appliances according to the methods of the present invention utilizing digital data sets representing the intermediate and final appliance designs.

Once the intermediate and final data sets have been created, the appliances may be fabricated as illustrated in FIG. 10. Preferably, fabrication methods will employ a rapid prototyping device 200 such as a stereolithography machine. A particularly suitable rapid prototyping machine is Model SLA-250/50 available from 3D System, Valencia, Calif. The rapid prototyping machine 200 will selectively harden a liquid or other non-hardened resin into a three-dimensional structure which can be separated from the remaining non-hardened resin, washed, and used either directly as the appliance or indirectly as a mold for producing the appliance. The prototyping machine 200 will receive the individual digital data sets and produce one structure corresponding to each of the desired appliances. Generally, because the rapid prototyping machine 200 may utilize a resin having non-optimum mechanical properties and which may not be generally acceptable for patient use, it will be preferred to use the prototyping machine to produce molds which are, in effect, positive tooth models of each successive stage of the treatment. After the positive models are prepared, a conventional pressure or vacuum molding machine may he used to produce the appliances from a more suitable material, such as 0.03 inch thermal forming dental material, available from Tru-Tain Plastics, Rochester, Minn. 55902. Suitable pressure molding equipment is available under the tradename BIOSTAR from Great Lakes Orthodontics, Ltd., Tonawanda, N.Y. 14150. The molding machine 250 produces each of the appliances directly from the positive tooth model and the desired material. Suitable vacuum molding machines are available from Raintree Essix, Inc.

After production, the plurality of appliances which comprise the system of the present invention are preferably supplied to the treating professional all at one time. The appliances will be marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

Figure 11:
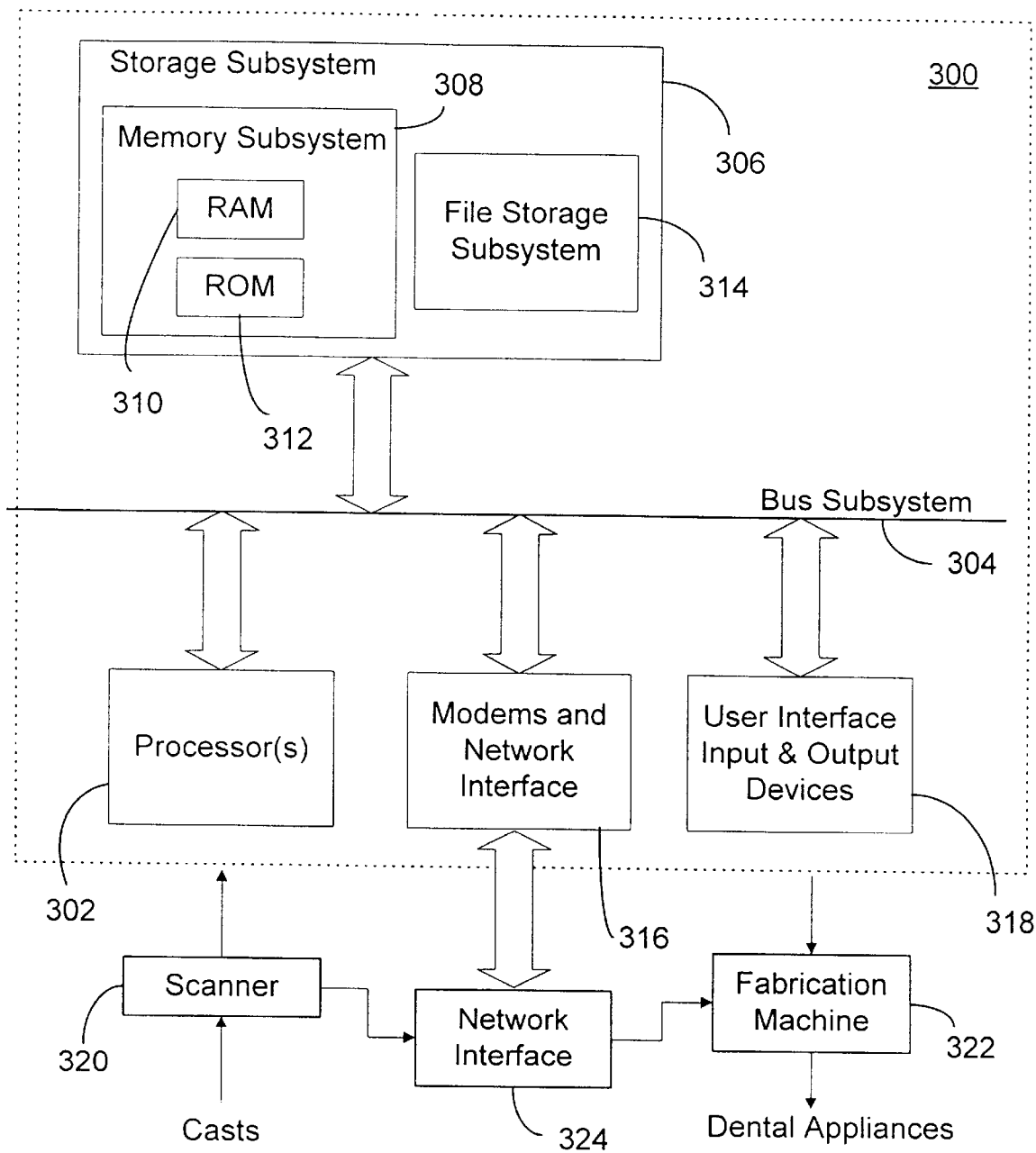
FIG. 11 is a simplified block diagram of a data processing system incorporating an embodiment of the present invention.

FIG. 11 is a simplified block diagram of a data processing system 300 embodying the present invention. Data processing system 300 typically includes at least one processor 302 which communicates with a number of peripheral devices via bus subsystem 304. These peripheral devices typically include a storage subsystem 306 (memory subsystem 308 and file storage subsystem 314), a set of user interface input and output devices 318, and an interface to outside networks 316, including the public switched telephone network. This interface is shown schematically as "Modems and Network Interface" block 316, and is coupled to corresponding interface devices in other data processing systems via communication network interface 324. Data processing system 300 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, are also possible.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 306 maintains the basic programming and data constructs that provide the functionality of the present invention. The software modules discussed above are typically stored in storage subsystem 306. Storage subsystem 306 typically comprises memory subsystem 308 and file storage subsystem 314.

Memory subsystem 308 typically includes a number of memories including a main random access memory (RAM) 310 for storage of instructions and data during program execution and a read only memory (ROM) 312 in which fixed instructions are stored. In the case of Macintosh-compatible personal computers the ROM would include portions of the operating system; in the case of IBM-compatible personal computers, this would include the BIOS (basic input/output system).

File storage subsystem 314 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is display need not be at the same location as the processor, although it is anticipated that the present invention will most often be implemented in the context of PCs and workstations.

Bus subsystem 304 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 320 is responsible for scanning casts of the patient's teeth obtained either from the patient or from an orthodontist and providing the scanned digital data set information to data processing system 300 for further processing. In a distributed environment, scanner 320 may be located at a remote location and commuicate scanned digital data set information to data processing system 300 via network interface 324.

Fabrication machine 322 fabricates dental appliances based on intermediate and final data set information received from data processing system 300. In a distributed environment, fabrication machine 322 may be located at a remote location and receive data set information from data processing system 300 via network interface 324.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for repositioning teeth from an initial tooth arrangement to a final tooth arrangement, said system comprising a plurality of dental incremental position adjustment appliances including:
   a first appliance having a geometry selected to reposition the teeth from the initial tooth arrangement to a first intermediate arrangement;
   one or more intermediate appliances having geometries selected to progressively reposition the teeth from the first intermediate arrangement to successive intermediate arrangements; and
   a final appliance having a geometry selected to progressively reposition the teeth from the last intermediate arrangement to the final tooth arrangement, wherein at least some of the appliances are marked to indicate their order of use.

2. A system as in claim 1, wherein the appliances comprise polymeric shells having cavities shaped to receive and resiliently reposition teeth from one arrangement to a successive arrangement.

3. A system as in claim 2, wherein the tooth positions defined by the cavities in each successive appliance differ from those defined by the prior appliance by no more than 2 mm.

4. A system as in claim 1, comprising at least two intermediate appliances.

5. A system as in claim 4, comprising at least ten intermediate appliances.

6. A system as in claim 5, comprising at least twenty-five intermediate appliances.

7. A system as in claim 1, wherein the appliances are marked with sequential numbering directly on the appliances.

8. A system as in claim 1, wherein the appliances are marked on tags which are affixed to the appliances.

9. A system as in claim 1, wherein the appliances are marked by placement in a pouch.

10. A system as in claim 1, further comprising instructions which set forth that the patient is to wear the individual appliances in the order marked on the appliance.

11. A method for repositioning teeth from an initial tooth arrangement to a final tooth arrangement, said method comprising:
    placing a first incremental position adjustment appliance in a patient's mouth, wherein the first appliance has a geometry selected to reposition the teeth from the initial tooth arrangement to a first intermediate arrangement;
    successively replacing one or more additional appliances, wherein the additional appliances have geometries selected to progressively reposition the teeth from the first intermediate arrangement to successive intermediate arrangements; and placing a final appliance into the patient's mouth, wherein the final appliance has a geometry selected to progressively reposition the teeth from the last intermediate arrangement to the final tooth arrangement, wherein at least some of the appliances are marked to indicate their order of use.

12. A method as in claim 11, wherein the appliances comprise polymeric shells having cavities shaped to receive and resiliently reposition teeth from one arrangement to a successive arrangement.

13. A method as in claim 12, where the tooth positions defined by the cavities in each successive appliance differ from those defined by the prior appliance by no more than 2 mm.

14. A method as in claim 11, wherein the successively placing step comprises placing at least two additional appliances prior to placing the final appliance.

15. A method as in claim 14, wherein the successively placing step comprises placing at least ten additional appliances.

16. A method as in claim 15, wherein the successively placing step comprises placing at least twenty-five additional appliances.

17. A method as in claim 11, wherein the appliances are successively replaced at an interval in the range from 2 days to 20 days.

18. A method as in claim 11, wherein the appliances are marked with sequential numbering directly on the appliances.

19. A method as in claim 11, wherein the appliances are marked on tags which are affixed to the appliances.

20. A method as in claim 11, wherein the appliances are marked by placement in a pouch.

21. A method for producing a plurality of digital data sets representing a series of discrete tooth arrangements progressing from an initial to a final arrangement, said method comprising:

providing a computer system having at least once processor and memory;

providing to the computer system an initial digital data set representing an initial tooth arrangement;

providing to the computer system a final digital data set representing a final tooth arrangement;

producing a plurality of successive digital data sets based on both of the provided initial and final digital data sets, wherein said plurality of digital data sets represent a series of successive tooth arrangements progressing from the initial tooth arrangement to the final tooth arrangement; and annotating the data sets to add text or numbering.

22. A method as in claim 21, wherein the step of providing a digital data set representing an initial tooth arrangement comprises scanning a three-dimensional model of a patient's teeth.

23. A method as in claim 21, wherein the step of providing a digital data set representing a final tooth arrangement comprises:

defining boundaries about at least some of the individual teeth on a visual image provided by the computer system; and moving at least some of the tooth boundaries relative to the other teeth in the visual image to produce the final data set.

24. A method as in claim 21, wherein the step of producing a plurality of successive digital data sets comprises determining positional differences between the initial data set and the final data set and interpolating said differences.

25. A method as in claim 24, wherein the interpolating step comprises linear interpolation.

26. A method as in claim 24, wherein the interpolating step comprises non-linear interpolation.

27. A method as in claim 24 further comprising defining one or more key frames between the initial tooth arrangement and final tooth arrangement and interpolating between the key frames.

28. A method as in claim 21, wherein annotating comprises adding a sequence number to the data set.

29. A method for fabricating a plurality of dental incremental position adjustment appliances, said method comprising:

providing an initial digital data set representing an initial tooth arrangement;

providing a final digital data set representing a final tooth arrangement;

producing a plurality of successive digital data sets based on both of the initial and final digital data sets, wherein said plurality of digital data sets represent a series of successive tooth arrangements progressing from the initial tooth arrangement to the final tooth arrangement;

annotating the data sets to add text or numbering;

fabricating appliances based on at least some of the produced digital data sets, wherein the text or numbering appears on the appliances.

30. A method as in claim 29, wherein the step of providing a digital data set representing an initial tooth arrangement comprises scanning a three-dimensional model of a patient's teeth.

31. A method as in claim 29, wherein the step of providing a digital data set representing a final tooth arrangement comprises:

defining boundaries about at least some of the individual teeth; and moving at least some of the tooth boundaries relative to the other teeth in an image based on the digital data set to produce the final data set.

32. A method as in claim 29, wherein the step of producing a plurality of successive digital data sets comprises determining positional differences between the initial data set and the final data set and interpolating said differences.

33. A method as in claim 32, wherein the interpolating step comprises linear interpolation.

34. A method as in claim 32, wherein the interpolating step comprises non-linear interpolation.

35. A method as in claim 32, further comprising defining one or more key frames between the initial tooth arrangement and final tooth arrangement and interpolating between the key frames.

36. A method as in claim 29, wherein the fabricating step comprises:

controlling a fabrication machine based on the successive digital data sets to produce successive positive models of the successive tooth arrangements; and producing the dental appliance as a negative of the positive model.

37. A method as in claim 36, wherein the controlling step comprises:

providing a volume of non-hardened polymeric resin; and scanning a laser to selectively harden the resin in a shape based on the digital data set to produce the positive model.

38. A method as in claim 36, wherein the producing step comprises modeling the appliance over the positive model.

39. A method as in claim 29, wherein annotating comprises adding a sequence number to the data set.

40. A method as in claim 39, wherein the numbers appearing on the final appliance indicate the appliance's order of use.

41. A method for fabricating a dental appliance, said method comprising:
providing a digital data set representing a modified tooth arrangement for a patient, said data set including text or numbering;
controlling a fabrication machine based on the digital data set to produce a positive model of the modified tooth arrangement, wherein the text or numbering appears on the positive model; and
producing the dental appliance as a negative of the positive model, wherein the text or numbering appears on the dental appliance.

42. A method as in claim 41, wherein the controlling step comprises:
providing a volume of non-hardened polymeric resin;
scanning a laser to selectively harden the resin in a shape based on the digital data set to produce the positive model.

43. A method as in claim 41, wherein the producing step comprises molding the appliance over the positive model.

44. A method as in claim 41, wherein a plurality of dental appliances are fabricated and wherein the text or numbering indicates an order of use.

45. A method for fabricating a dental appliance, said method comprising:
providing a first digital data set representing a modified tooth arrangement for a patient;
producing a second digital data set from the first data set, wherein the second data set represents a negative model of the modified tooth arrangement; and
controlling a fabrication machine based on the second digital data set to produce the dental appliance, wherein the appliance is marked with text or data.

46. A method as in claim 45, wherein the controlling step comprises selectively hardening a non-hardened resin to produce the appliance and separating the appliance from the remaining liquid resin.

47. A method as in claim 45, wherein the appliance comprises a polymeric shell having a cavity shaped to receive and resiliently reposition teeth from an initial tooth arrangement to the modified tooth arrangement.

48. A method as in claim 45, wherein a plurality of dental appliances are fabricated and wherein the text or numbering indicates an order of use.

49. A method for fabricating a plurality of dental incremental position adjustment appliances, said method comprising:
providing digital data representing a plurality of successive tooth arrangements progressing from an initial tooth arrangement to a final tooth arrangement, said data including text or numbering; and
controlling a fabrication machine based on the digital data to produce the appliances, wherein the text or numbering appears on the appliance.

50. A method as in claim 49, wherein providing the digital data comprises providing a plurality of digital data sets, wherein each set represents one of the successive tooth arrangements, and wherein the text or numbering indicates an order of use.

51. A method as in claim 50, wherein the fabrication machine is controlled to produce polymeric shell appliances.

52. A method as in claim 49, wherein controlling the fabrication machine comprises:
providing a volume of non-hardened polymeric resin; and
selectively hardening the resin in a shape corresponding to each of the appliances.

53. A method as in claim 52, wherein selectively hardening comprises scanning a laser to selectively cross-link the resin.

54. A method as in claim 52, wherein controlling the fabrication machine comprises:
providing a volume of non-hardened polymeric resin; and
selectively hardening the resin in a shape corresponding to each of the appliances.

55. A method as in claim 54, wherein hardening comprises scanning a laser to selectively cross-link the resin.

56. A method as in claim 54, wherein scanning produces an appliance comprising a thin polymeric shell.

57. A method as in claim 52, wherein scanning produces an appliance comprising a thin polymeric shell.

58. A method of fabricating a plurality of dental incremental position adjustment appliances, said method comprising:
providing a plurality of positive models of successive tooth arrangements, wherein each successive arrangement represents a stage progressing from an initial tooth arrangement to an intermediate or a final tooth arrangement and wherein said models have printed annotations; and
fabricating the plurality of dental appliances as negatives of the positive models, wherein the annotations appear on the dental appliances.

59. A method as in claim 58, wherein the annotations comprise sequential numbering indicating an order of use.

60. A method as in claim 59, wherein providing said positive models comprises:
providing digital data representing said plurality of successive tooth arrangements; and
controlling a fabrication machine to produce said plurality of positive models of successive tooth arrangements.

61. A method as in claim 60, wherein providing digital data comprises producing a plurality of digital data sets, wherein each set represents one of the successive tooth arrangements.

62. A method as in claim 61, wherein controlling the fabrication machine comprises:
providing a volume of non-hardened polymeric resin; and
scanning a laser to selectively harden the resin in a shape corresponding to each of the positive models.

63. A method as in claim 60, wherein controlling the fabrication machine comprises:
providing a volume of non-hardened polymeric resin; and
scanning a laser to selectively harden the resin in a shape corresponding to each of the positive models.

64. A method as in claim 58, wherein producing the dental appliances comprises molding a thin polymeric sheet over each of the positive models to produce a plurality of thin polymeric shells.

65. A method of fabricating one or more dental incremental position adjustment appliances, comprising:
providing a computer generated positive model of at least one tooth arrangement selected from an initial tooth arrangement, an intermediate tooth arrangement, and final tooth arrangement, wherein said models have printed annotations; and
fabricating at least one dental appliance as a negative of the computer generated positive model, wherein the annotations appear on the dental appliances.

66. A method as in claim 65, wherein the annotations comprise sequential numbering indicating an order of use.

67. A method as in claim 65, wherein providing said at least one positive model comprises:

provide digital data representing at least one tooth arrangement; and controlling a fabrication machine to produce 'said at least one positive model of a tooth arrangement.

68. A method as in claim 67, wherein providing digital data comprises producing a plurality of digital data sets, wherein each set represents one of a plurality of successive tooth arrangements.

69. A method as in claim 68, wherein controlling the fabrication machine comprises:

providing a volume of non-hardened polymeric resin; and scanning a laser to selectively harden the resin in a shape corresponding to each of the positive models.

70. A method as in claim 67, wherein controlling the fabrication machine comprises:

providing a volume of non-hardened polymeric resin; and scanning a laser to selectively harden the resin in a shape corresponding to each of the positive models.

71. A method as in claim 65, wherein fabricating the at least one dental appliance comprises molding a thin polymeric sheet over said at least one positive model to produce at least one thin polymeric shells.

* * * * *

(12) EX PARTE REEXAMINATION CERTIFICATE (6014th)
United States Patent
Muhammad et al.

(10) Number: US 6,398,548 C1
(45) Certificate Issued: *Nov. 20, 2007

(54) METHOD AND SYSTEM FOR INCREMENTALLY MOVING TEETH

(75) Inventors: Chishti Muhammad, Sunnyvale, CA (US); Apostolos Lerios, Austin, TX (US); Brian Freyburger, Palo Alto, CA (US); Kelsey Wirth, Palo Alto, CA (US); Richard Ridgley, Los Altos, CA (US)

(73) Assignee: Align Technology, Inc., Santa Clara, CA (US)

Reexamination Request:
No. 90/007,510, Apr. 15, 2005

Reexamination Certificate for:
Patent No.: 6,398,548
Issued: Jun. 4, 2002
Appl. No.: 09/466,353
Filed: Dec. 17, 1999

(*) Notice: This patent is subject to a terminal disclaimer.

Related U.S. Application Data

(63) Continuation of application No. PCT/US98/12861, filed on Jun. 19, 1998, and a continuation of application No. 08/947,080, filed on Oct. 8, 1997, now Pat. No. 5,975,893.
(60) Provisional application No. 60/050,342, filed on Jun. 20, 1997.

(51) Int. Cl.
*A61C 3/00* (2006.01)

(52) U.S. Cl. .............................. 433/24; 433/6
(58) Field of Classification Search ........................ None
See application file for complete search history.

(56) References Cited

U.S. PATENT DOCUMENTS

| | | | |
|---|---|---|---|
| 2,467,432 A | 4/1949 | Kesling | |
| 3,407,500 A | 10/1968 | Kesling | |
| 3,600,808 A | 8/1971 | Reeve | |
| 3,683,502 A | 8/1972 | Wallshein | |
| 3,916,526 A | 11/1975 | Schudy | |
| 3,922,788 A | 12/1975 | Lavin | |
| 3,950,851 A | 4/1976 | Bergersen | |
| 3,983,628 A | 10/1976 | Acevedo | |
| 4,014,096 A | 3/1977 | Dellinger | |
| 4,195,046 A | 3/1980 | Kesling | |
| 4,253,828 A | 3/1981 | Coles et al. | |
| 4,324,546 A | 4/1982 | Heitlinger et al. | |
| 4,324,547 A | 4/1982 | Arcan et al. | |
| 4,348,178 A | 9/1982 | Kurz | |
| 4,478,580 A | 10/1984 | Barrut | |
| 4,500,294 A | 2/1985 | Lewis | |
| 4,504,225 A | 3/1985 | Yoshii | |
| 4,526,540 A | 7/1985 | Dellinger | |
| 4,575,330 A | 3/1986 | Hull | |
| 4,575,805 A | 3/1986 | Moermann et al. | |
| 4,591,341 A | 5/1986 | Andrews | |
| 4,609,349 A | 9/1986 | Cain | |

(Continued)

FOREIGN PATENT DOCUMENTS

| | | |
|---|---|---|
| AU | 3031677 | 5/1979 |
| AU | 5598894 | 6/1994 |
| CA | 1121955 | 4/1982 |

(Continued)

OTHER PUBLICATIONS

Declaration of Richard Ridgley, Mar. 16, 2005, total pages 5.

(Continued)

*Primary Examiner*—Michael O'Neill

(57) ABSTRACT

A system for repositioning teeth comprises a plurality of individual appliances. The appliances are configured to be placed successively on the patient's teeth and to incrementally reposition the teeth from a initial tooth arrangement, through a plurality of intermediate tooth arrangements, and to a final tooth arrangement. The system of appliances is usually configured at the outset of treatment so that the patient may progress through treatment without the need to have the treating professional perform each successive step in the procedure.

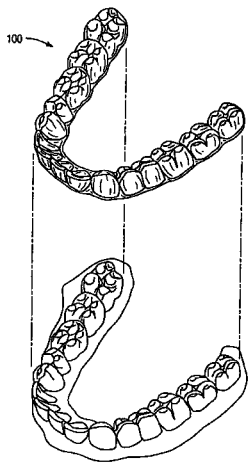

U.S. PATENT DOCUMENTS

| | | |
|---|---|---|
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,763,791 A | 8/1988 | Halverson et al. |
| 4,793,803 A | 12/1988 | Martz |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,027,281 A | 6/1991 | Rekow et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,257,203 A | 10/1993 | Riley et al. |
| 5,278,756 A | 1/1994 | Lemchen et al. |
| 5,368,478 A | 11/1994 | Andreiko et al. |
| 5,440,326 A | 8/1995 | Quinn |
| 5,440,496 A | 8/1995 | Andersson et al. |
| RE35,169 E | 3/1996 | Lemchen et al. |
| 5,518,397 A | 5/1996 | Andreiko et al. |
| 5,528,735 A | 6/1996 | Strasnick et al. |
| 5,562,448 A | 10/1996 | Mhabac |
| 5,614,075 A | 3/1997 | Andre |
| 5,621,648 A | 4/1997 | Crump |
| 5,645,420 A | 7/1997 | Bergersen |
| 5,655,653 A | 8/1997 | Chester |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,524,101 B1 | 2/2003 | Phan |
| 6,554,611 B2 | 4/2003 | Chishti et al. |
| 6,629,840 B2 | 10/2003 | Chishti et al. |
| 6,705,863 B2 | 3/2004 | Phan et al. |
| 2002/0006597 A1 | 1/2002 | Andreiko et al. |

FOREIGN PATENT DOCUMENTS

| | | |
|---|---|---|
| DE | 2749802 | 5/1978 |
| DE | 69327661 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0667753 | 8/1995 |
| EP | 0774933 B1 | 5/1997 |
| EP | 0541500 A1 | 6/1998 |
| EP | 0731673 B1 | 9/1998 |
| ES | 0463897 | 1/1980 |
| FR | 2652256 A1 | 3/1991 |
| GB | 1550777 | 8/1979 |
| JP | 53-058191 | 5/1978 |
| JP | 0428359 | 1/1992 |
| JP | 04028359 * | 1/1992 |
| JP | 08-508174 | 9/1996 |
| WO | WO 90/08512 A1 | 8/1990 |
| WO | WO 91/04713 A1 | 4/1991 |
| WO | WO 98/32394 | 7/1998 |
| WO | WO 98/44865 A1 | 10/1998 |
| WO | WO 98/58596 A1 | 12/1998 |

OTHER PUBLICATIONS

Deposition Transcript of Lloyd Truax, D.D.S., Case No. SACV:03–16 GLT(ANX), *Ormco Corporation v. Align Technology, Inc.,* (Dec. 3, 2004), total pp. 51.

Deposition Transcript of Kevin L. Truax, Case No. SACV:03–16 GLT(ANX), *Ormco Corporation v. Align Technology, Inc.,* (Dec. 3, 2004), total pp. 57.

Documents produced by Lloyd and Kevin Truax, Case No. SACV:03–16 GLT(ANX), *Ormco Corporation v. Align Technology, Inc.,* total pp. 63.

Deposition Transcript of Michael David Rains, D.D.S., Case No. SACV:03–16 GLT(ANX), *Ormco Corporation v. Align Technology, Inc.,* (Nov. 15, 2004), total pp. 57.

Deposition Transcript of Michael David Rains, D.D.S., Case No. SACV:03–16 GLT(ANX), *Ormco Corporation v. Align Technology, Inc.,* (Nov. 15, 2004), total pp. 14.

Documents produced by Guadalupe Nieto, Case No. SACV:03–16 GLT(ANX), *Ormco Corporation v. Align Technology, Inc.,* total pp. 33.

Alcaniz, et al., "An Advanced System for the Stimulation and Planning of Orthodontic Treatments," Visualization in Biomedical Computing, Eds. Hohne and Kikinis, Springer–Verlag (Sep. 1996), pp. 511–520.

Andrews, "Straight Wire, The Concept and Appliance," The Six Keys to Optimal Occlusion, Chapter 3, pp. 13–24.

Bartels, et al., An introduction to Splines for Use in Computer Graphics and Geometric Modeling, Morgan Kaufmann Publishers (1987), 422–425.

Biggerstaff, "Computerized Diagnostic Setups and Simulations," The Angle Orthodontist, vol. 40, No. 1 (Jan. 1970), pp. 28–36.

Blu, et al., "Linear Interpolation Revitalized", IEEE Transactions on Image Processing (May 2004), vol., No. 13(5), pp. 710–719.

Cardinal Industrial Finishes, Powder Coatings information posted at http://www.cardinalpaint.com on Aug. 25, 2000, 6 pages total.

Curry et al., "Integrated Three–Dimensional Craniofacial Mapping at the Craniofacial Research Instrumentation Laboratory/University of the Pacific," Seminars in Orthodontics, vol. 7, No. 4 (Dec. 2001), pp. 258–265.

Defranco et al., "Three–Dimensional Large Displacement Analysis of Orthodontic Appliances," J. Biomechanics, vol. 9 (1976), pp. 793–801.

Dentrac Corporation, Dentrac document, pp. 4–13.

DENT–X posted at http://www.dent-x.com/DentSim.htm, Sep. 24, 1998, 6 pages total.

Doyle, "Digital Dentistry," Computer Graphics World (Oct. 2000), pp. 50–52, 54.

Duret et al., "CAD–CAM in Dentistry," Journal of the American Dental Association, vol. 117, No. 6 (Nov. 1988), pp. 715–720.

Fütterling et al., "Automated Finite Element Modeling of a Human Mandible with Dental Implants," WSCG '98—Conference Program, retrieved from the Internet: <<http://wscg.zcu.cz/wscg98/papers98/Strasser_98.pdf.>>, 8 pages total.

Hikage, "Integrated Orthodontic Management System for Virtual Three–Dimensional Computer Graphic Simulation and Optical Video Image Database for Diagnosis and Treatment Planning", Journal of Japan Orthodontic Society (Feb. 1987), English translation, pp. 1–34, Japanese version, vol. 46, pp. 248–269 (56 pages total).

Hojjatie et al., "Three–Dimensional Finite Element Analysis of Glass–Ceramic Dental Crowns," J. Biomech. (1990), vol. 23, No. 11, pp. 1157–1166.

Xochanek et al., "Interpolating Splines with Local Tension, Continuity, and Blas Control", Computer Graphics (Jul. 1984), vol. 18(3), pp. 33–41.

Kunii et al., "Articulation Simulation for an Intelligent Dental Care System," Displays, vol. 15, No. 3 (1994), pp. 181–188.

Procera Research Projects, Procera Research Projects 1993—Abstract Collection (1993), pp. 3–24.

Proffit et al., Contemporary Orthodontics (Second Ed.), Chapter 15, The First Stage of Comprehension Treatment: Alignment and Levelling, Mosby Inc. (Oct. 1992), pp. 470–533.

Redmond et al., "Clinical Implications of Digital Orthodontics," Am. J. Orthodont. and Dentofacial Orthopedics, vol. 117, No. 2 (2000), pp. 240–242.

Rekow et al., "CAD/CAM for Dental Restorations—Some of the Curious Challenges," IEEE Transactions on Biomedical Engineering (Apr. 1991), vol. 38, No. 4, pp. 314–318.

Rekow et al., "Comparison of Three Data Acquisition Techniques for 3–D Tooth Surface Mapping," Annual International Conference of the IEEE Engineering in Medicine and Biology Society (1991), vol. 13, No. 1, pp. 344–345.

Rekow, "Feasibility of an Automated System for Production of Dental Restorations," PhD Thesis, Univ. of Minnesota, Nov. 1988, 250 pages total.

Richmond et al., "The Development of the PAR Index (Peer Assessment Rating): Reliability and Validity," European Journal of Orthodontics (1992), vol. 14, pp. 125–139.

Schroeder et al., Eds. Chapters 6, 8, 9, The Visual Toolkit (1996), pp. 153–209, 309–353, and 355–427, respectively.

Sturman, "Interactive Keyframe Animation of 3–D Articulated Models," Proceedings Graphics Interface '84 (May–Jun. 1984), pp. 35–40.

Tru–Tain Orthodontic & Dental Supplies, Product Brochure, Rochester, Minnesota 55902, 16 pages total.

Van Der Zel, "Ceramic–Fused–to–Metal Restorations With a New CAD/CAM System," Quintessence International, vol. 24:11, (Nov. 1993), pp. 769–778.

Alexander et al., "The DigiGraph Work Station Part 2, Clinical Management," JCO (Jul. 1990), pp. 402–407.

Altschuler et al., "Measuring Surfaces Space–Coded by a Laser–Projected Dot Matrix," SPIE: Imaging Applications for Automated Industrial Inspection and Assembly, vol. 182 (1979), p. 187–191.

Altschuler et al., "Analysis of 3–D Data for Comparative 3–D Serial Growth Pattern Studies of Oral–Facial Structures," IADR Abstracts #510, Program and Abstracts of Papers, 57th General Session, IADR Annual Session, Mar. 29, 1979–Apr. 1, 1979, New Orleans Marriot, Journal of Dental Research, vol. 58, Jan. 1979, Special Issue A, p. 221.

Altschuler et al., "Laser Electro–Optic System for Rapid Three–Dimensional (3D) Topographic Mapping of Surfaces," Optical Engineering, vol. 20(6) (1981), pp. 953–961.

Altschuler, "3D Mapping of Maxillo–Facial Prosthesis," AADR Abstracts #607 (1980), 1 page total.

American Association for Dental Research, Summary of Activities, Mar. 20–23, 1980, Los Angeles, CA, p. 195.

Andersson et al., "Clinical Results with Titanium Crowns Fabricated with Machine Duplication and Spark Erosion," Acta Odontological Scandinavia, vol. 47 (1989), pp. 279–286.

Baumrind et al., "A Stereophotogrammetric System for the Detection of Prosthesis Loosening in Total Hip Arthroplasty," NATO Symposium on Applications of Human Biostereometrics (Jul. 9–13, 1978), SPIE, vol. 166, pp. 112–123.

Baumrind et al., "Mapping the Skull in 3–D," Reprinted from The Journal, California Dental Association, vol. 48, No. 2 (1972 Fall Issue), 11 pages total.

Baumrind, "A System for Craniofacial Mapping Through the Integration of Data from Stereo X–Ray Films and Stereo Photographs," An invited paper submitted to the 1975 American Society of Photogram. Symposium on Close–Range Photogram Systems, University of Il. (Aug. 26–30, 1975), pp. 142–166.

Baumrind, "Integrated Three–Dimensional Craniofacial Mapping: Background, Principles, and Perspectives," Seminars in Orthodontics, vol. 7, No. 4 (Dec. 2001), pp. 223–232.

Begole et al., "A Computer System for the Analysis of Dental Casts," The Angle Orthodontist, vol. 51, No. 3 (Jul. 1981), pp. 252–258.

Bernard et al., "Computerized Diagnosis in Orthodontics for Epidemiological Studies: A Progress Report," Abstracts of Papers #449, Journal of Dental Research; vol. 67, Special Issue Mar. 9–13, 1988, J3. p. 169.

Bhatia et al., "A Computer–Aided Design for Orthognathic Surgery," British Journal of Oral and Maxillofacial Surgery, vol. 22 (1984), pp. 237–253.

Biggerstaff et al., "Computerized Analysis of Occlusion in the Postcanine Dentition, American Journal of Orthodontics," vol. 61, No. 3 (Mar. 1972), pp. 245–254.

Boyd et al., "Three Dimensional Diagnosis and Orthodontic Treatment of Complex Malocclusions With the Invisalign Appliance," Seminars in Orthodontics, vol. 7, No. 4 (Dec. 2001), pp. 274–293.

Brandestini et al., "Computer Machined Ceramic Inlays: In Vitro Marginal Adaptation," Journal of Dental Research, vol. 64/Special Issue/Abstracts, IADR/AADR Abstracts #305 (1985), p. 208.

Brook et al., "An Image Analysis System for the Determination of Tooth Dimensions from Study Casts: Comparison with Manual Measurements of Mesio–distal Diameter," J Dent Res., vol. 65, No. 3 (Mar. 1986), pp. 428–431.

Burstone (Interview), "Dr. Charles J. Burnstone on The Uses of the Computer in Orthodontic Practice (Parts 1and 2)," Journal of Clinical Orthodontics, (Part 1) vol. 13, No. 7, pp. 442–453, Jul. 1979; (Part 2) vol. 13, No. 8 pp. 539–551, Aug. 1979.

Burnstone et al., "Precision adjustment of the transpalatal lingual arch: Computer arch from predetermination," Am. Journal of Orthodontics, vol. 79, No. 2 (Feb. 1981), pp. 115–133.

Chaconas et al., "The DigiGraph Work Station, Part 1, Basic Concepts," JCO (Jun. 1990), pp. 360–367.

Chafetz et al., "Subsidence of the Femoral Prosthesis, A Stereophotogrammetric Evaluation," Clinical Orthopaedics and Related Research, No. 201 (Dec. 1985), pp. 60–67.

Crawford, "CAD/CAM in the Dental Office: Does It Work?" Canadian Dental Journal, vol. 57, No. 2 (Feb. 1991), pp. 121–123.

Crawford, "Computers in Dentistry: Part 1: CAD/CAM: The Computer Moves Chairside," "Part 2: F. Duret—A Man With A Vision," "Part 3: The Computer Gives New Vision—Literally," "Part 4: Bytes 'N Bites" The Computer Moves From The Front Desk To The Operatory, Canadian Dental Journal, vol. 54(9), (1988), pp. 661–666.

Crooks, "CAD/CAM Comes to USC," USC Dentistry (Spring 1990), pp. 14–17.

Cutting et al., "Three–Dimensional Computer–Assisted Design of Craniofacial Surgical Procedures: Optimization and Interaction with Cephalometric and CT–Based Models," Plastic and Reconstructive Surgery, vol. 77, No. 6 (Jun. 1986), pp. 877–875.

DCS Dental AG, "The CAD/CAM 'DCS Titan System' for Production of Crowns/Bridges" DSC Production AG (Jan. 1992), pp. 1–7.

Dental Institute University of Zurich Switzerland, Program for International Symposium on Computer Restorations: State of the Art of the CEREC–Method, May 1991, 2 pages total.

Duret et al., "CAD/CAM Imaging in Dentistry," Current Opinion in Dentistry, vol. 1 (1991), pp. 150–154.

Duret, "The Dental CAD/CAM, General Description of the Project," Hennson International Product Brochure (Jan. 1986), 18 pages total.

Duret, "Vers Une Prosthese Informatisee," (English translation also attached), Tonus, vol. 73, (Nov. 15, 1985), pp. 55–57.

Economides, "The Microcomputer in the Orthodontic Office," JCO (Nov. 1979), pp. 767–772.

Faber et al., "Computerized interactive orthodontic treatment planning," Am. J. Orthod., vol. 73, No. 1 (Jan. 1978), pp. 36–46.

Felton et al., "A Computerized Analysis of the Shape and Stability of Mandibular Arch Form," Am. Journal of Orthodontics and Dentofacial Orthopedics, vol. 92, No. 6 (Dec. 1987), pp. 478–483.

Friede et al., "Accuracy of Cephalometric Prediction in Orthognathic Surgery," Abstract of Papers, Journal of Dental Research, vol. 70 (1987), pp. 754–760.

GIM–ALLDENT Deutschland, "Das DUX System: Die Technik," 2 pages total.

Grayson, "New Methods for Three Dimensional Analysis of Craniofacial Deformity," Symposium: Computerized Facial Imaging in Oral and Maxillofacial Surgery, Presented on Sep. 13, 1990, AAOMS 72nd Annual Meeting and Scientific Sessions, Sep. 13, 1990, New Orleans, Journal of Oral and Maxillofacial Surgery, vol. 48, No. 8, Supp. 1, Aug. 1990, pp. 5–6.

Guess et al., "Computer Treatment Estimates In Orthodontics and Orthognathic Surgery," JCO (Apr. 1989), pp. 262–268.

Heaven et al., "Computer–based Image Analysis of Artificial Root Surface Caries" "Automated Identification of Landmarks in Cephalometric Radiographs," Abstracts of Papers #2094, Journal of Dental Research, vol. 67 (Mar. 9–13), 1 page total.

Hoffmann et al., "Role of Cephalometry for Planning of Jaw Orthopedics and Jaw Surgery Procedures," (Article Summary In English, article in German), Informationen (Mar. 1991), pp. 375–396.

Huckins, "CAD–CAM Generated Mandibular Model Prototype from MRI Data," AAOMS 1999, p. 96.

JCO Interviews, "Craig Andreiko, DDS, MS on the Elan and Orthos Systems," JCO (Aug. 1994), pp. 459–468.

JCO Interviews, "Dr. Homer W. Phillips on Computers in Orthodontic Practice, Part 2," JCO (Dec. 1983), pp. 819–831.

Jerrold, "The Problem, Electronic Data Transmission and the Law," AJO–DO (Arp. 1988), pp. 478–479.

Jones et al., "An Assessment of the Fit of a Parabolic Curve to Pre– and Post–Treatment Dental Archers," British Journal of Orthodontics, vol. 16 (1989), pp. 85–93.

Kanazawa et al., "Three–Dimensional Measurements of the Occlusal Surfaces of Upper Molars in a Dutch Population." J Dent Res, vol. 63, No. 11 (Nov. 1984), pp. 1298–1301.

Laurendeau et al., "A Computer–Vision Technique for the Acquisition and Processing of 3–D Profiles of Dental Imprints: An Application in Orthodontics," IEEE Transactions on Medical Imaging, vol. 10, No. 3 (Sep. 1991), pp. 453–461.

Leinfelder et al., "A New Method for Generating Ceramic Restorations: A CAD–CAM System," Journal Of The American Dental Assoc. vol. 118, No. 6 (Jun. 1989), pp. 703–707.

Manetti et al., "Computer–aided Cefalometry and New Mechanics in Orthodontics," (Article Summary in English, article in German), Fortsch. Kieferorthop. 44, 370–376 (Nr. 5), 1983.

McCann, Inside the ADA, Journal Of The American Dental Assoc., vol. 118 (Mar. 1989) pp. 286–294.

McNamara et al., "Invisible Retainers," J. Clinical Orthodontics (Aug. 1985), pp. 570–578.

McNamara et al., Chapter 19: Invisible Retainers. Orthodontic and Orthopedic Treatment in the Mixed Dentition, Needham Press, Jan. 1993, pp. 347–353.

Moermann et al., "Computer Machined Adhesive Porcelain Inlays: Margin Adaptation after Fatigue Stress," IADR Abstract #339, Journal of Dental Research, vol., No. 66(a) (1987), p. 763.

Mormann et al., "Marginal Adaptation Von Adhesive Porzellanintays in Vitro," *Schwizerische Monatsshrift fur Zahnmedizin,* vol. 95 (1985), pp. 1118–1129.

Nash, "Cerec CAD/CAM Inlays: Aesthetics and Durability in a Single Appointment," Dentistry Today (Oct. 1990), pp. 20, 22–23, 54.

Pinkham, "Foolish' Concept Propels Technology," Dentist, Jan./Feb. 1989, 3 pages total.

Pinkham, "Inventor's CAD/CAM May Transform Dentist," Dentistry (Sep. 1990), 3 pages total.

Rekow, "A Review of the Developments in Dental CAD/CAM Systems," (contains references to Japanese efforts and content of the papers of particular interest to the clinician are indicated with a one–line summary of their content in the bibliography), Dental Clinics: Prosthodontics and Endodontics, pp. 25–33, 1992.

Rekow, "CAD/CAM in Dentistry: A Historical Perspective and View of the Future," Journal, vol. 58, No. 4 (Apr. 1992), pp. 283, 287–288.

Rekow, "Computer–Aided Design and Manufacturing in Dentistry: A Review of the State of the Art," The Journal of Prosthetic Dentistry, vol. 28, No. 4 (Oct. 1987), pp. 512–516.

Rekow, "Dental CAD–CAM Systems: What is the State of the Art?" Journal of the American Dental Assoc., vol. 122 (1991), pp. 43–48.

Richmond et al., Research Reports, "The Development of a 3D Cast Analysis System," British Journal of Orthodontics, vol. 13, No. 1, (Jan. 1986), pp. 53–54.

Richmond, "Recording the Dental Cast in Three Dimensions," Am. J. Orthod. Dentofac. Orthop., vol. 92, No. 3 (Sep. 1987), pp. 199–206.

Rudge, "Dental Arch Analysis: Arch Form, A Review of the Literature," European Journal of Orthodontics, vol. 3, No. 4 (1981), pp. 279–284.

Sakuda et al., "Integrated Information–Processing System In Clinical Orthodontics: An Approach With Use of a Computer Network System," Am. J. Orthod. Dentofac. Orthop., vol. 101, No. 3 (Mar. 1982), pp. 210–220.

Schellhas et al., "Three–Dimensional Computed Tomography in Maxillofacial Surgical Planning," Arch Otolarmgol Head Neck Surg. vol. 114 (Apr. 1988), pp. 438–442.

Siemens, "CEREC—Computer–Reconstruction, High Tech in der Zahnmedizin," 14 page total.

Sirona Dental Systems GmbH, CEREC 3D, Manuel Utilisateur, Version 2.0X (in French), 2003, 114 pages total.

Stoll et al., "Computer–aided Technologies in Dentistry," (Article Summary in English, article in German), Dtsch Zahnärztl Z 45, 314–322, 1990.

U.S. Department of Commerce, National Technical Information Service, "Automated Crown Replication Using Solid Photography SM," Solid Photography Inc. Melville NY, Oct. 1977, 19 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Provisional Appl. No. 60/050,342, filed Jun. 20, 1997, 27 pages total.

Van Der Linden et al., "Three–Dimensional Analysis of Dental Casts by Means of the Optocom," J Dent Res, Jul.–Aug. 1972, p. 1100.

Van Der Linden, "A New Method to Determine Tooth Positions and Dental Arch Dimensions," Jul.–Aug. 1972, p. 1104.

Varady et al., "Reverse Engineering of Geometric Models—An Introduction, Computer–Aided Design," 29 (4):255–268, 1997, (May 1996), pp. 1–28.

Williams, "Dentistry and CAD/CAM: Another French Révolution," Journal of Dental Practice Admin. (Jan./Mar. 1987), pp. 2–5.

Williams, "The Switzerland and Minnesota Developments in CAD/CAM," Journal of Dental Practice Admin. (Apr./Jun. 1987), pp. 50–55.

Wishan, "New Advances in Personal Computer Applications for Cephalometric Analysis, Growth Prediction, Surgical Treatment Planning and Imaging Processing," Symposium: Computerized Facial Imaging in Oral and Maxillofacial Surgery, Presented on Sep. 13, 1990, AAOMS 72nd Annual Meeting and Scientific Sessions, Sep. 13, 1990, New Orleans, Journal of Oral and Maxillofacial Surgery, vol. 48, No. 8, Supp. 1, Aug. 1990, p. 5.

Yamamoto et al., "Optical Measurement of Dental Cast Profile and Application to Analysis of Three–Dimensional Tooth Movement in Orthodontics," Frontliners in Med. and Biol. Eng'g, vol. 1, No. 2 (1988), pp. 119–130.

Yamamoto et al., "Three–Dimensional Measurement of Dental Cast Profiles and Its Applications to Orthodontics," Proceedings of the Twelfth Annual Int'l Conf. of IEEE Engineering in Medicine and Biology Society, vol. 12, No. 5 (1990), pp. 2051–2053.

Nahoum, H. I. (Nov. 1964). "The vacuum formed dental contour appliance," *The New York State Dental Journal* 30(9): 385–390.

Ponitz, R. J. (Mar. 1971). "Invisible retainers," *Am. J. Orthod.* 59 (3): 266–72.

Gottleib and McNamara. (Jun. 1982). "JCO Interviews Dr. James A. McNamara, Jr., on the Frankel Appliance, Part 2: Clinical Management," *Journal of Clinical Orthodontics* 16(6): 390–407.

Sinclair, Peter M. (Jun. 1992). "The Readers' Corner," *Journal of Clinical Orthodontics* 26(6): 369–372.

Warunek et al. (May 1989). "Physical and mechanical properties of elastomers in orthodontic positioners," *Am. J. Orthod. Dentofac. Orthop.* 95(5): 388–400.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 11, lines 41–43:

Based on both the IDDS and the FDDS, a plurality of intermediate digital data sets (INTDDS's) are generated to correspond to *successive intermediate tooth arrangements. The system of incremental position adjustment appliances can then be fabricated based on the INTDDS's, as described in more detail below.*

AS A RESULT OF REEXAMINATION, IT HAS BEEN DETERMINED THAT:

The patentability of claims 21–71 is confirmed.

Claims 1, 3, 11 and 13 are determined to be patentable as amended.

Claims 2, 4–10, 12 and 14–20, dependent on an amended claim, are determined to be patentable.

New claims 72–94 are added and determined to be patentable.

1. A system for repositioning teeth from an initial tooth arrangement to a final tooth arrangement, said system comprising a plurality of dental incremental position adjustment appliances including:
   a first appliance having a *teeth receiving cavity* geometry selected to reposition the teeth from the initial tooth arrangement to a first intermediate arrangement;
   one or more intermediate appliances having *teeth receiving cavity* geometries selected to progressively reposition the teeth from the first intermediate arrangement to successive intermediate arrangements, *wherein the teeth receiving cavity geometry of an intermediate appliance differs from the teeth receiving cavity geometry of another appliance of the system*; [and]
   a final appliance having a *teeth receiving cavity* geometry selected to progressively reposition the teeth from the last intermediate arrangement to the final tooth arrangement wherein at least some of the appliances are marked to indicate their order of use; *and*
   *wherein at least two of the appliances comprise successive appliances that have differing successive teeth receiving cavity geometries and that are each fabricated prior to the use of either of them for treatment.*

3. A system as in claim 2, wherein the tooth positions defined by the cavities in each successive appliance differ from those defined by the prior appliance by no more than [2] *0.5* mm *and wherein, prior to the fabrication of the appliances, computer software is used to determine whether the differences between successive tooth positions of successive tooth arrangements do not exceed predetermined limits defined in the software.*

11. A method for repositioning teeth from an initial tooth arrangement to a final tooth arrangement, said method comprising:
    placing a first incremental position adjustment appliance in a patient's mouth, wherein the first appliance has a *teeth receiving cavity* geometry selected to reposition the teeth from the initial tooth arrangement to a first intermediate arrangement;
    successively replacing one or more additional appliances, wherein the additional appliances have *teeth receiving cavity* geometries selected to progressively reposition the teeth from the first intermediate arrangement to successive intermediate arrangements, *wherein the teeth receiving cavity geometry of an intermediate appliance differs from the teeth receiving cavity geometry of another of the appliances placed in the patient's mouth*; [and]
    placing a final appliance into the patient's mouth, wherein the final appliance has a *teeth receiving cavity* geometry selected to progressively reposition the teeth from the last intermediate arrangement to the final tooth arrangement, wherein at least some of the appliances are marked to indicate their order of use; *and*
    *fabricating at least two of said appliances, wherein said at least two appliances comprise successive appliances that have differing successive teeth receiving cavity geometries, said fabricating being accomplished for at least said two appliances before either of said two appliances is placed into the patient's mouth.*

13. A method as in claim 12, where the tooth positions defined by the cavities in each successive appliance differ from those defined by the prior appliance by no more than [2] *0.5* mm.

*72. A method for repositioning teeth of a patient from an initial tooth arrangement to a final tooth arrangement, said method comprising:*
    *producing a plurality of digital data sets representing sequential tooth arrangements for a patient, the producing step comprising:*
        *(a) producing a digital data set representing at least one of a successive intermediate tooth arrangement and a final tooth arrangement;*
        *(b) after step (a), producing a digital data set representing a preceeding intermediate tooth arrangement;*
    *fabricating a plurality of dental incremental position adjustment appliances based on the digital data sets;*
    *placing a first incremental position adjustment appliance in the patient's mouth, wherein the first appliance has a teeth receiving cavity geometry based on one of the digital data sets and selected to reposition the teeth from the initial tooth arrangement to a first intermediate arrangement;*
    *successively replacing one or more additional appliances, wherein the additional appliances have teeth receiving cavity geometries selected to progressively reposition the teeth from the first intermediate arrangement to successive intermediate arrangements, each such additional appliance having a teeth receiving cavity geometry based on a separate one of the digital data sets; and*
    *placing a final appliance into the patient's mouth, wherein the final appliance has a teeth receiving cavity* geometry selected to progressively reposition the teeth from the last intermediate arrangement to the final tooth arrangement, wherein the appliances comprise polymeric shells having cavities shaped to receive and resiliently reposition teeth from one arrangement to a successive arrangement, and wherein at least some of the appliances are marked to indicate their order of use.

73. *The method of claim 72, wherein said step (a) of producing further comprises producing a digital data set representing a successive intermediate tooth arrangement prior to producing a digital data set representing a preceding intermediate tooth arrangement.*

74. *The method of claim 72 wherein said final tooth arrangement is produced by adjusting representations of the patient's teeth to positions defined by a treating professional in a prescription for the patient.*

75. *The method of claim 72 wherein said step of producing a plurality of digital data sets also comprises:*
   *producing a digital data set representing an initial tooth position, and*
   *producing a digital data set representing at least one of a successive intermediate tooth arrangement and a final tooth arrangement by manipulating images of the teeth of the initial tooth position to arrive at the intermediate or final tooth arrangement.*

76. *The method of claim 72 wherein each of said additional appliances has a different teeth receiving cavity geometry.*

77. *The method as in claim 72, wherein a plurality of the appliances are capable of being provided to the patient at the outset of treatment.*

78. *A system for repositioning teeth from an initial tooth arrangement to a final tooth arrangement for a patient, said system comprising:*
   *a plurality of digital data sets, each of said digital data sets representing a successive tooth arrangement for the patient; and*
   *a plurality of dental incremental position adjustment appliances including:*
   *a first appliance having a teeth receiving cavity geometry based on one of the digital data sets and selected to reposition the patient's teeth from the initial tooth arrangement to a first intermediate arrangement;*
   *one or more intermediate appliances having teeth receiving cavity geometries selected to progressively reposition the patient's teeth from the first intermediate arrangement to successive intermediate arrangements, each such intermediate appliance having a teeth receiving cavity geometry based on a separate digital data set; and*
   *a final appliance having a geometry selected to progressively reposition the patient's teeth from the last intermediate arrangement to the final tooth arrangement, wherein the appliances comprise polymeric shells having cavities, wherein the cavities of successive shells have different geometries shaped to receive and resiliently reposition teeth from one arrangement to a successive arrangement, and wherein at least some of the appliances are marked to indicate their order of use.*

79. *The system of claim 78, wherein two or more of the appliances comprise unused sequential appliances capable of being provided at one time to a patient.*

80. *The system of claim 78, wherein two or more of the appliances comprise unused sequential appliances capable of being provided at one time to a dental practitioner.*

81. *The system of claim 78, wherein the plurality of the appliances are capable of being provided to the patient at the outset of treatment.*

82. *A method for repositioning teeth of a patient from an initial tooth arrangement to a final tooth arrangement, said method comprising:*
   *providing an initial tooth arrangement of a patient including an initial tooth position for a tooth of the patient;*
   *defining a key frame intermediate tooth position for the tooth;*
   *after the defining step, generating at least one additional intermediate tooth position sequentially positioned between the initial tooth position and the key frame tooth position;*
   *incorporating the key frame intermediate tooth position and the at least one additional intermediate tooth position into respective data sets, each such data set representing an intermediate tooth arrangement for the patient;*
   *fabricating, based on the data sets, a plurality of incremental position adjustment appliances, each appliance comprising a polymeric shell having a unique teeth receiving cavity geometry selected to receive and resiliently reposition the patient's teeth from one arrangement to a successive tooth arrangement;*
   *placing a first incremental position adjustment appliance in the patient's mouth, wherein the first appliance has said teeth receiving cavity geometry selected to reposition the teeth from the initial tooth arrangement to a first intermediate arrangement;*
   *successively replacing one or more additional appliances, wherein the additional appliances have teeth receiving cavity geometries selected to progressively reposition the teeth from the first intermediate arrangement to successive intermediate arrangements and wherein such additional appliances include at least one appliance fabricated based on one of the data sets; and*
   *placing a final appliance into the patient's mouth, wherein the final appliance has a teeth receiving cavity geometry selected to progressively reposition the teeth from the last intermediate arrangement to the final tooth arrangement, wherein at least some of the appliances are marked to indicate their order of use.*

83. *The method of claim 82 further comprising:*
   *defining a key frame intermediate tooth position for a second tooth;*
   *after the defining step for the second tooth, generating for the second tooth at least one intermediate tooth position sequentially positioned between the initial tooth position and the key frame tooth position or between the key frame tooth position and a subsequent sequential tooth position;*
   *incorporating for the second tooth, the key frame intermediate tooth position and the at least one intermediate tooth position into respective data sets, each such data set representing an intermediate tooth arrangement and fabricating an appliance based on each such data set.*

84. *The method of claim 82 wherein the key frame intermediate tooth position is provided by the treating professional as a prescription.*

85. *The method as in claim 82, wherein a plurality of the appliances are capable of being provided to the patient at the outset of treatment.*

86. *A method for repositioning teeth from an initial tooth arrangement to a final tooth arrangement, said method comprising:* generating a treatment plan that maps the movement paths of selected teeth of a patient using at least in part computer operated software,

*wherein the step of generating a treatment plan includes computing the length of the movement path of at least one tooth as a step to avoid moving that tooth significantly more than necessary in said treatment plan,*

*wherein such treatment plan serves to move the tooth toward a target position while avoiding interferences between teeth, and* wherein said generating step further comprises generating a plurality of successive tooth arrangements;

fabricating a plurality of sequential appliances based on the successive tooth arrangements, wherein the appliances comprise polymeric shells having cavities, wherein the cavities of successive shells have different geometries shaped to receive and resiliently reposition teeth from one arrangement to a successive arrangement;

placing a first incremental position adjustment appliance of said fabricated appliances in the patient's mouth, wherein the first appliance has a teeth receiving cavity geometry selected to reposition the teeth from the initial tooth arrangement to a first intermediate arrangement;

successively replacing one or more additional appliances of said fabricated appliances in the patient's mouth, wherein the additional appliances have teeth receiving cavity geometries selected to progressively reposition the teeth from the first intermediate arrangement to successive intermediate arrangements; and placing a final appliance into the patient's mouth, wherein the final appliance has a geometry selected to progressively reposition the teeth from the last intermediate arrangement to the final tooth arrangement, wherein at least some of the sequential appliances are marked to indicate their order of use.

87. *The method of claim 86, wherein the step of generating a treatment plan comprises:*

*generating a plurality of unobstructed tooth movement paths for a selected tooth;*

*computing the length of each of the tooth movement paths; and*

*selecting the shortest unobstructed tooth movement path for the selected tooth.*

88. *The method as in claim 86, wherein a plurality of the appliances are capable of being provided to the patient at the outset of treatment.*

89. *A method for repositioning teeth of a patient from an initial tooth arrangement to a final tooth arrangement, said method comprising:*

*fabricating a plurality of sequential incremental position adjustment appliances, each appliance comprising a polymeric shell having a teeth receiving cavity geometry selected to receive and resiliently reposition the patient's teeth from one arrangement to a successive arrangement,*

*packaging the appliances;*

*providing the appliances to one of the patient and a treatment professional;*

*after said fabricating, packaging, and supplying steps, placing a first one of the incremental position adjustment appliances in the patient's mouth, wherein the first appliance has a teeth receiving cavity geometry selected to reposition the teeth from the initial tooth arrangement to a first intermediate arrangement;*

*successively replacing one or more additional ones of the appliances, wherein the additional appliances have teeth receiving cavity geometries selected to progressively reposition the teeth from the first intermediate arrangement to successive intermediate arrangements and wherein the teeth receiving cavity geometry of one of the intermediate appliances differs from the teeth receiving cavity geometry of another of the appliances placed in the patient's mouth; and*

*placing a final appliance into the patient's mouth, wherein the final appliance has a teeth receiving cavity geometry selected to progressively reposition the teeth from the last intermediate arrangement to the final tooth arrangement, wherein at least some of the appliances are marked to indicate their order of use.*

90. *A system for repositioning teeth from an initial tooth arrangement to a final tooth arrangement, said system comprising a plurality of dental incremental position adjustment appliances including:*

*a first appliance having a teeth receiving cavity geometry selected to reposition the teeth from the initial tooth arrangement to a first intermediate arrangement;*

*one or more intermediate appliances having teeth receiving cavity geometries selected to progressively reposition the teeth from the first intermediate arrangement to successive intermediate arrangements;*

*a final appliance having a teeth receiving cavity geometry selected to progressively reposition the teeth from the last intermediate arrangement to the final tooth arrangement wherein at least some of the appliances are marked to indicate their order of use;*

*wherein a plurality of the appliances have different teeth receiving cavity geometries; and*

*wherein two or more of the appliances comprise successive appliances capable of being provided at one time to a patient or dental practitioner prior to the use of any of the provided appliances in treatment of the patient.*

91. *The system of claim 90, wherein at least some of the appliances are marked to indicate to a patient their order of use.*

92. *The system of claim 1, wherein two or more of the fabricated appliances can be provided at one time to a patient or dental practitioner prior to their use in treatment.*

93. *The system of claim 78, wherein the tooth positions defined by the teeth receiving cavity geometry in each successive appliance differ from those defined by the prior appliance by no more than 0.5 mm and wherein, prior to fabricating the appliances, computer software is used to determine whether the differences between successive tooth positions of successive tooth arrangements do not exceed predetermined limits defined in the software.*

94. *The system of claim 90, wherein the tooth positions defined by the teeth receiving cavity geometry in each successive appliance differ from those defined by the prior appliance by no more than 0.5 mm and wherein, prior to fabricating the appliances, computer software is used to determine whether the differences between successive tooth positions of successive tooth arrangements do not exceed predetermined limits defined in the software.*

\* \* \* \* \*